(12) United States Patent
Warren et al.

(10) Patent No.: US 11,978,543 B2
(45) Date of Patent: May 7, 2024

(54) SYSTEM AND METHODS FOR DEVELOPING AND USING A MICROBIOME-BASED ACTION COMPONENT

(71) Applicant: Astarte Medical Partners Inc., Yardley, PA (US)

(72) Inventors: Tracy Warren, Pennington, NJ (US); Arti Tandon, Wayland, MA (US)

(*) Notice: Subject to any disclaimer, the term of this patent is extended or adjusted under 35 U.S.C. 154(b) by 555 days.

(21) Appl. No.: 17/074,173

(22) Filed: Oct. 19, 2020

(65) Prior Publication Data

US 2021/0050080 A1 Feb. 18, 2021

Related U.S. Application Data

(63) Continuation-in-part of application No. 15/842,346, filed on Dec. 14, 2017, now Pat. No. 10,811,126.
(Continued)

(51) Int. Cl.
*G16H 15/00* (2018.01)
*G16H 10/60* (2018.01)
(Continued)

(52) U.S. Cl.
CPC ............ *G16H 15/00* (2018.01); *G16H 10/60* (2018.01); *G16H 20/60* (2018.01); *G16H 50/20* (2018.01);
(Continued)

(58) Field of Classification Search
CPC .... G06F 1/00–2221/2153; G16H 10/00–80/00
See application file for complete search history.

(56) References Cited

U.S. PATENT DOCUMENTS 9,058,627 B1   6/2015  Wasser et al.
2004/0214148 A1  10/2004  Salvino et al.
(Continued)

FOREIGN PATENT DOCUMENTS

WO    2011130546 A1   10/2011

OTHER PUBLICATIONS

Perez-Cobas et al., "Gut microbiota disturbance during antibiotic therapy: a multi-omic approach," Gut 2013; 62:1591-1601. doi: 10.1136/gutjnl-2012-303184. (Year: 2013).*
(Continued)

*Primary Examiner* — Jonathon A. Szumny
(74) *Attorney, Agent, or Firm* — Valauskas Corder LLC

(57) ABSTRACT

The invention relates generally to a system and methods by which a microbiome-based action component may be developed that is useful in order to establish, restore, promote, or maintain subject health. More specifically, the system and methods of the present invention may be used to develop a microbiome-based action component that efficiently summarizes the state of a subject's microbiome along with measures of gut maturity in case of an infant and nutrition readiness in case of an adult subject. Such an efficient summary may be used to render more immediate support or health care to the subject. Certain specific embodiments of the present invention may be used to facilitate the development a microbiome-based action component that provides, in addition to the efficient summary, a subject-specific, personalized microbiome health plan that includes options that may be followed in order that the subject may achieve personal health, growth, and development goals given the state of the subject's microbiome and state of maturity or nutritional readiness by aligning appropriate decision-making to the individual microbiome-based profile of the subject.

11 Claims, 14 Drawing Sheets

Related U.S. Application Data

(60) Provisional application No. 62/433,990, filed on Dec. 14, 2016.

(51) Int. Cl.
*G16H 20/60* (2018.01)
*G16H 50/20* (2018.01)
*G16H 50/30* (2018.01)
*G16H 50/70* (2018.01)
*G16H 70/20* (2018.01)
*G06F 3/14* (2006.01)

(52) U.S. Cl.
CPC ............ *G16H 50/30* (2018.01); *G16H 50/70* (2018.01); *G16H 70/20* (2018.01); *G06F 3/14* (2013.01)

(56) References Cited

U.S. PATENT DOCUMENTS

| | | | |
|---|---|---|---|
| 2004/0249675 A1 | 12/2004 | Stark et al. | |
| 2006/0135610 A1* | 6/2006 | Bortz | A61K 31/355 514/548 |
| 2008/0167262 A1 | 7/2008 | Cooney et al. | |
| 2008/0255069 A1 | 10/2008 | Shudo et al. | |
| 2010/0004213 A1 | 1/2010 | Abbas et al. | |
| 2010/0015156 A1 | 1/2010 | Dubinsky | |
| 2010/0331641 A1* | 12/2010 | Bangera | A61B 5/0002 702/19 |
| 2012/0171672 A1 | 7/2012 | Barken et al. | |
| 2012/0296675 A1 | 11/2012 | Silverman | |
| 2013/0035951 A1 | 2/2013 | Frey | |
| 2013/0225439 A1 | 8/2013 | Princen et al. | |
| 2014/0004105 A1* | 1/2014 | Perlee | C12Q 1/6883 424/133.1 |
| 2014/0179726 A1 | 6/2014 | Baja et al. | |
| 2014/0314719 A1 | 10/2014 | Smith | |
| 2014/0358587 A1 | 12/2014 | Cao et al. | |
| 2015/0054930 A1* | 2/2015 | Bangera | G06V 20/693 348/77 |
| 2015/0093725 A1* | 4/2015 | Baarman | G09B 5/00 600/300 |
| 2015/0227710 A1* | 8/2015 | Pappada | G16H 70/20 705/2 |
| 2016/0071393 A1 | 3/2016 | Kaplan et al. | |
| 2016/0139148 A1 | 5/2016 | Westin et al. | |
| 2016/0178644 A1 | 6/2016 | Hackney et al. | |
| 2016/0216274 A1 | 7/2016 | Kain et al. | |
| 2016/0245786 A1 | 8/2016 | Collino et al. | |
| 2016/0266147 A1 | 9/2016 | Loktionov et al. | |
| 2016/0314281 A1 | 10/2016 | Apte et al. | |
| 2017/0132357 A1* | 5/2017 | Brewerton | G16B 50/00 |
| 2017/0172167 A1* | 6/2017 | Silver | A23C 9/206 |
| 2017/0202925 A1 | 7/2017 | Couvineau et al. | |
| 2017/0205429 A1 | 7/2017 | Figeys et al. | |
| 2018/0010187 A1 | 1/2018 | Lyons et al. | |
| 2018/0022800 A1 | 1/2018 | West et al. | |
| 2018/0046774 A1 | 2/2018 | Lindahl et al. | |
| 2018/0064950 A1 | 3/2018 | Segal | |
| 2018/0180630 A1 | 6/2018 | Monteleone | |
| 2019/0021703 A1* | 1/2019 | Dominguez-Bello | A61B 10/0045 |
| 2019/0030096 A1 | 1/2019 | Cutcliffe et al. | |
| 2019/0136288 A1* | 5/2019 | Apte | G16B 10/00 |
| 2019/0178868 A1* | 6/2019 | Shortt | A61B 5/0002 |
| 2021/0395220 A1* | 12/2021 | Lascola | C07D 401/12 |

OTHER PUBLICATIONS

Rodriguez et al., "The composition of the gut microbiota throughout life, with an emphasis on early life," Microbial Ecology in Health & Disease 2015, 26: 26050—http://dx.doi.org/10.3402/mehd.v26.26050. (Year: 2015).*

Aujnarain et al., "The Role of the Environment in the Development of Pediatric Inflammatory Bowel Disease," Curr Gastroenterol Rep (2013) 15:326; DOI 10.1007/s11894-013-0326-4. (Year: 2013).*

Frese et al., "Diet shapes the gut microbiome of pigs during nursing and weaning," Microbiome (2015) 3:28; DOI 10.1186/s40168-015-0091-8. (Year: 2018).*

Cong et al., "Gut Microbiome Developmental Patterns in Early Life of Preterm Infants: Impacts of Feeding and Gender," PLoS One 11(4): e0152751; doi:10.1371/journal.pone.0152751. (Year: 2016).*

Cong et al., "Influence of Infant Feeding Type on Gut Microbiome Development in Hospitalized Preterm Infants," Nurs Res. 2017; 66(2): 123-133. doi:10.1097/NNR.0000000000000208. (Year: 2017).*

Bokulich et al., "Antibiotics, birth mode, and diet shape microbiome maturation during early life," Jun. 15, 2016, Science Translations Medicine, vol. 8, Issue 343 (2016).

Forslund et al., "Disentangling type 2 diabetes and metformin treatment signatures in the human gut microbiota ," Dec. 2015, Nature, vol. 528—dated Dec. 10, 2015.

* cited by examiner

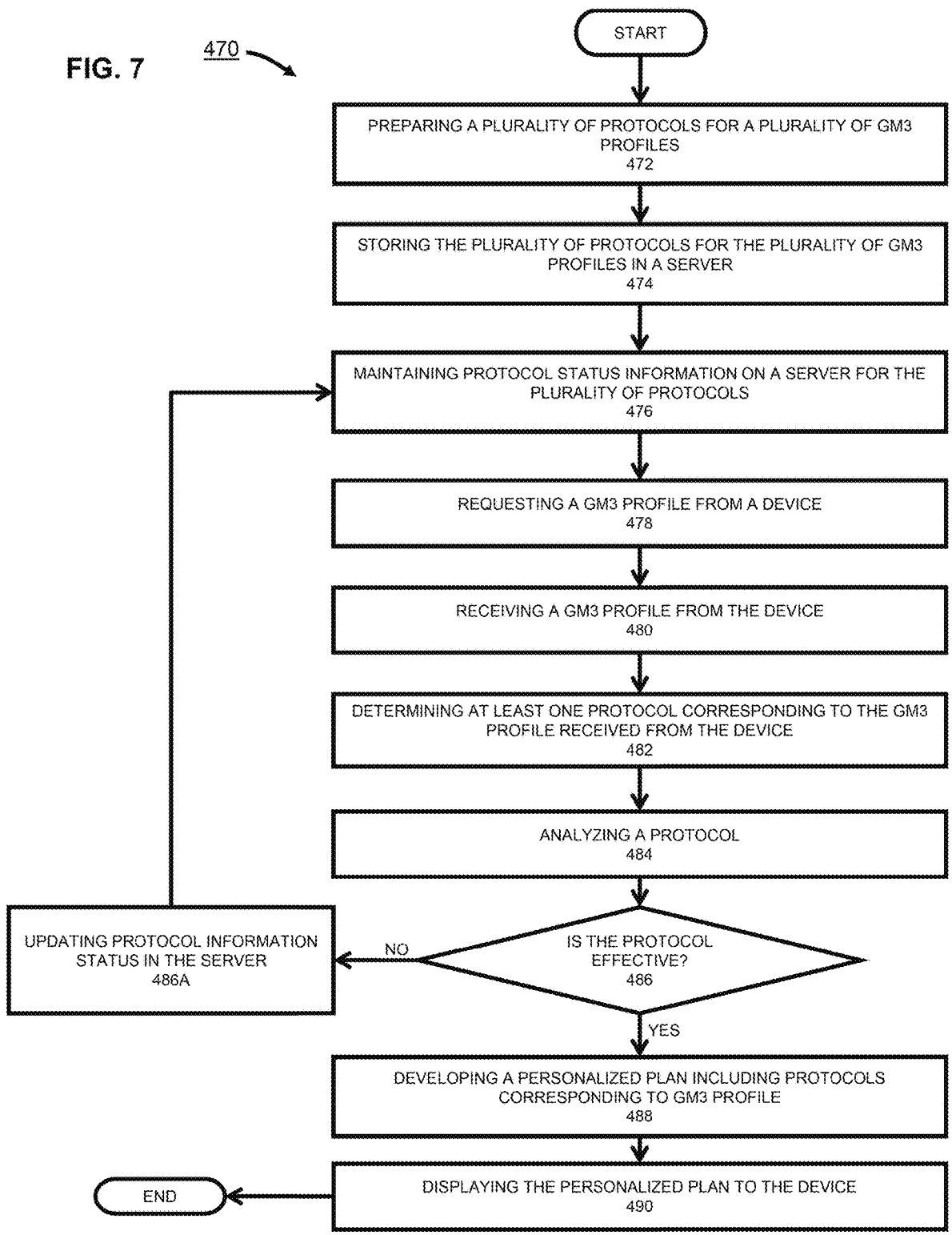

FIG. 10

| Risk Levels | | | Recommendation(s) |
| --- | --- | --- | --- |
| Maturity | Stability | Classification | |
| High | High | High | Advance feeds slowly; preference for mother's milk, introduce probiotic(s); only use human milk fortifier |
| High | High | Low | Advance feeds cautiously; introduce probiotic(s) |
| High | Low | High | Advance feeds cautiously; use mother's milk if available; add probiotic(s) to donor milk or formula |
| High | Low | Low | Advance feeds cautiously, use mothers milk if available |
| Low | High | High | Consider advancing feeds and potentially adding prebiotic(s) to create transitions |
| Low | High | Low | Consider advancing feeds and potentially introducing prebiotic(s) to create transitions |
| Low | Low | High | Consider prebiotic(s) to alter classification |
| Low | Low | Low | Consider advancing feeds more aggressively; prebiotic(s) |

890

SYSTEM AND METHODS FOR DEVELOPING AND USING A MICROBIOME-BASED ACTION COMPONENT

CROSS REFERENCE TO RELATED PATENTS

This application is a continuation-in-part application of U.S. application Ser. No. 15/842,346 filed Dec. 14, 2017, now U.S. Pat. No. 10,811,126, which claims the benefit of U.S. Provisional Patent Application No. 62/433,990 filed Dec. 14, 2016, which is incorporated by reference.

FIELD OF INVENTION

The field of invention relates generally to a system and methods that may be used to develop a microbiome-based action component useful to establish, promote, or maintain a subject's health. More specifically, the system and methods of the present invention may be used to develop a microbiome-based action component that efficiently summarizes the state of a subject's gut microbiome and the related influences of nutrition, diet, adverse events and microbial-based interventions, including antibiotics, pre and probiotics. Such an efficient summary may be used to render more immediate nutrition selection and decision making such as health care to the subject. Certain specific embodiments of the present invention may be used to develop a microbiome-based action component that provides, in addition to the efficient summary, a subject-specific, personalized microbiome health plan that includes options that may be followed in order that the subject may achieve personal health, growth, and development goals given the state of the subject's gut microbiome.

BACKGROUND OF THE INVENTION

A microbe is a single-celled or multicellular microscopic living organism. There are six main types of microbes: archaea, bacteria, fungi, protozoa, viruses, and algae. Microbes live in practically every part of the biosphere and are found everywhere in and on the human body, including the nasal passages, oral cavities, skin, gastrointestinal tract, and the urogenital tract. The term "microbiota" refers to a community of commensal, symbiotic, and/or pathogenic microbes. The term "microbiome" refers to the full collection of microbes and the genetic information of those microbes within a specific body area (the "habitat") of the host.

Each type of microbe may produce a different effect in the context in which the microbe comes to live. The composition of the microbiota that may reside on and within, for example, a mammalian organism may affect immune function, nutrient processing, and other aspects of physiology. The composition of the microbiota may change over time and can be affected by age, diet, antibiotic exposure, and other environmental influences. When different microbial species produce largely the same effect, the microbiota is said to have some functional redundancy. An addition or loss of microbial species that produce similar effects may have little influence on the overall effect that the microbiota has on the physiology of the mammalian system. However, the addition or loss of certain microbial species, even if present in small numbers, may produce a significant effect on mammalian physiology.

Microbiota acquisition during the early years of life can have long-lasting effects on long-term development. It is known that the infant gut microbiota undergoes a period of immense change during the early years of life. Microbiota adapts over time and is shaped by the availability of different nutrients. In an infant's community, a stable microbiota develops that resembles that of an adult.

The first exposure to microorganisms occurs during delivery. The microbiota of vaginal births differs from that of caesarean (C-) section deliveries. Diet also contributes to microbiota. In addition, environment including the people and animals that are around the infant are also sources of microorganisms. Also, genetics has a role in determining microbiota make-up. Antimicrobials and antibiotics can impact microbiota in infants. Regardless, microbiota is critical in immune, metabolic, endocrine development of infants. These factors, alone and in combination, affect microbiota in a plethora of ways. For example, good nutrition in an immature environment may be just as insufficient as poor nutrition in an age-appropriate infant, i.e. a healthy gut.

When the microbial species that produce what is considered to be a beneficial effect on the system are not at least equal to the microbial species that produce what is considered to be a harmful effect on the system, a microbial imbalance is said to have been created. "Dysbiosis" refers to the state in which a system has an imbalance in the beneficial and harmful microbes. Dysbiosis can occur when there is a low diversity of beneficial microbial species and/or a lack of functional redundancy of beneficial microbes in the microbiota.

What is considered to be a healthier system may be established or reestablished by limiting the harmful microbes while promoting the development of the beneficial microbes. The term "eubiosis" refers to the state in which the beneficial microbes within a system have a dominant effect because there is a high diversity and/or a functional redundancy of the beneficial microbial species in the system.

Throughout the animal kingdom, females can transfer microbes to a fetus before birth and to their offspring during the course of and after birth. Several factors, including mode of birth, the environment in which the birth takes place, and manner of feeding and diet can influence the precise microbial community associated with a newborn. In addition to factors relevant to labor and birth, females can transfer microbes to a fetus and to their offspring in many ways. For example, microbes can become associated with a fetus in the prenatal phase. The placenta harbors a variety of microbes to which the fetus is exposed. As the fetus passes through the birth canal, it is exposed to the microbes of the mother's vagina. After birth, skin-to-skin contact can transfer microbes from parents/caregivers to an infant. Also, microbes in breast milk are passed to the infant during feeding. All such early exposures to microbes influence the developing immune system of the infant, and ultimately affect the individual's health throughout childhood and later in life.

The fetus and newborn develop certain microbial communities depending on whether the child is born preterm versus after a full-term pregnancy. Premature infants, as a result of the early birth, have a microbial community that is highly influenced by the shorter gestation period and the hospital environment where life-saving intensive care is rendered to the infant following birth. The microbiome of such infants is often less fully developed, or biologically immature, and may include the harmful or pathogenic species found in the hospital environment. An underdeveloped microbiota—or one in which it is "stunted" by repeated exposure to antibiotics—in an infant may lead to a dominance of pathogenic microbes and thus cause diseases. For example, premature infants in a dysbiotic state may develop a serious gastrointestinal infection called necrotizing enterocolitis ("NEC"). NEC is just one example of the many adverse health outcomes that are associated with early microbial and immune-mediated mechanisms.

Given the long term impact on growth and neurodevelopmental outcomes, there are many advantages in analyzing which microbes are associated with infants at an early age in order, for example, to determine whether the infant may be suffering from a condition caused by harmful or pathogenic microbes—such as an unhealthy inflamed state—and whether the infant may be in a dysbiotic state.

The microbes associated with an infant or any subject can be identified in many ways. For example, certain microbial species that reside on and within a subject may be identified by collecting samples from the microbiota and culturing them in an appropriate culture media. Such a traditional culture-based method, however, can detect only those microbes that can be grown in vitro. As a result, other culture-independent methods, such as molecular genomic sequencing, have been developed to analyze the genetic material of a microbiota sample and detect those microbes that were previously undetectable by traditional, culture-based methods.

While many benefits can be realized from the analysis of a subject's microbial state, such analyses are not currently conducted as part of standard clinical care procedures. Current care protocols react to a subject's physical signs caused by conditions, including those caused by an imbalance of the subject's microbiota. Such reactive treatments for conditions caused by microbiota imbalances include withholding feedings, bowel rest, and antibiotic administration. These treatments often take time to produce results and may have many unintended risks associated with them for the subject.

Even when the microbial condition of a subject is identified, the important question of whether and to what extent the subject is nutritionally ready for intervention and specifically which interventions are appropriate for that subject may not be answered.

Treatment to improve, maintain, and advance the health condition of a subject could be more efficiently rendered if an efficient summary of the subject's microbial condition and gut maturity or nutrition readiness was available.

Furthermore, a comprehensive approach to the care of a subject that takes into account the subject's microbial state and their gut maturity or nutritional readiness and seeks to achieve a range of short-term and longer term, health-related objectives, such as promoting the growth and development of the subject through adequate/appropriate nutrition, would be advantageous to a subject.

However, any such microbiome-based action component has not been developed and, as a result, is not available for use as part of conventional standard of care protocols.

Accordingly, there is a need for a system and methods by which a microbiome-based action component may be developed and made available for use for subject health and that may be revised as the condition of the subject changes. The present invention satisfies this need.

SUMMARY OF THE INVENTION

The present invention relates generally to a system and methods that may be used to develop a microbiome-based action component useful to establish, promote, and maintain subject health. More specifically, the system and methods of the present invention may be used to develop a microbiome-based action component that efficiently summarizes the state or maturity of a subject's microbiome.

Such an efficient summary may be made accessible to a subject, a caregiver, or health care providers and used to render more immediate decisions such as that related to care and appropriate nutrition to the subject. Certain preferred embodiments of the present invention may be used to develop a microbiome-based action component that provides, in addition to the efficient summary, a subject-specific, personalized microbiome health plan that includes options that may be followed in order that the subject may achieve personal health, growth, and development goals given the state of the subject's microbiome. For purposes of this application, a "subject" is any mammal and may refer to an infant or adult. Illustrative examples in the following include those making reference to humans.

Certain preferred embodiments of the present invention permit a subject to supply some or all the data needed by the system to develop the microbiome-based action component, not only by entry of such information by the subject directly but also through the use of a device such as a wearable or insertable device that can communicate to the system and/or from other sources such as the subject's health records or personal device. Other preferred embodiments are intended to be used by the subject, a caregiver or a health care provider and permit such individual to incorporate information provided directly by the subject or from observations made, analyses conducted, nutritional interventions and/or treatments rendered by the health care provider or third parties and recorded such as in the health care or personal health records for the subject. For purposes of the application, entry of information into the system by either the subject directly or via a wearable device is contemplated to include, for example, keyboard entry, touchscreen, voice inputs or speech recognition, biometric inputs, to name a few.

In certain preferred embodiments of the invention, the system may be used to develop a microbiome-based action component that provides a summary or profile of the state of the subject's microbiome. This microbiome-based action component is a comprehensive measure of the gut maturity in case of infants and nutrition readiness in case of an older subject. Microbiome maturity measures or gut microbiome maturity measures ("GM3") may include microbiome, clinical, and personal information. These measures provide insight into gut maturity and are used to provide a profile so that gut maturity or nutritional readiness can be better understood. "Appropriate" is both measured within a person over time (self as reference) as well as versus a population-health type reference.

Early in life, an infant's microbiome has novel exposures, which may cause it to present fetal-like, unable to support and maintain communities of taxa that can demonstrate maturity or nutritional readiness. In early stages, the gut microbiome can be underdeveloped, immature or stunted by various actions, for example, malnutrition, antibiotics, etc. GM3 information is used to develop a profile referred to as a gut maturity or readiness profile", "gut maturity/readiness profile", or "GM3 profile").

In certain embodiments, this system uses GM3 information to develop the gut maturity or nutrition readiness profile through the following steps: identifying the subject; identifying the health risk factors for the subject; obtaining the clinical and biodemographic information of the subject; and making adjustments to the data if the subject is an infant. The system may update and revise the GM3 information as the data and other inputs change or as selections are made. From the GM3 information, the system develops a summary that allows the subject's microbiome state or status to be understood quickly and for treatment options to be selected.

In certain preferred embodiments, the above two steps may be followed by a third step in which an additional microbiome-based action component—a personalized microbiome health plan—may be created for the subject based on their gut maturity/readiness profile. This plan may identify options that a subject, a caregiver or a health care provider may follow to achieve subject-specific objectives. Among other options, a caregiver or health care provider may choose to develop a nutritional plan for the subject, recommend that the subject change or adopt a certain hygiene plan, modify sleep patterns, take steps to engage in certain exercise, and generally modify other behaviors. The plan may also identify options that a subject can follow independently.

According to certain embodiments, taxa are evaluated to determine which taxa play a role at each stage—developmental, transitional, stable—of the subject's gut development and at each transition between phases, or stages. It is also contemplated that the taxa is evaluated to explain the differences among stages. "Healthy" or most frequent stages are identified as well as pathways, or transitional patterns, against which subjects are measured.

A health plan may include a set of recommendations incorporating the various measures of gut status, including maturity, classification and stability. Microbiome analysis will inform a measure of gut maturity based on Microbiota for Age Z-score ("MAZ"), a temporal classification using Dirichlet Multinomial Mixtures ("DMM") reflecting the underlying microbiome community structure based on taxa, and a tracking of transitions among classifications, whether discrete or in total, as a measure of stability or lack thereof. Stability may also include other microbiome measures, such as variation in microbial communities between samples taken over time, as measured by standard measures, ex. beta diversity. Early in life, microbiome transitions have been associated with increased diversity and associated resilience or health.

Each of the modeling approaches may include confidence intervals for the prediction or classification. These measures are repeatedly calculated over time, and vary in their influence over the subject's life, through weighting factors. For example, in the first week of life, it is not anticipated that the stability measures are as influential given the short passage of time, whereas by day 30, stability can be better assessed. Similarly, MAZ converges with chronological age over time and with proper intervention, therefore decreasing its "weighting" or influence in the composite risk score. Classifications are made at discrete time points and over time the subject becomes his or her own reference as to which stages or clusters it has been classified into, over different time periods and how frequently.

More specifically regarding the collection and development of the GM3 information described above, the subject is identified such as by the entry of the subject's name, age, or other biodemographic information.

In certain preferred embodiments, the GM3 information is developed with the entry of microbial health risk factors. These factors are those conditions or events that may have produced the current microbial condition of the subject. Microbial health risk factors may include the subject's mode of birth (i.e. vaginal or cesarean section), exposure to antibiotics, and the nutrition that the subject is receiving.

The GM3 information may be developed through the entry of clinical information—such as the subject's physical condition, symptoms, and health risk factor information—such as by the subject directly, a caregiver/parent, and/or by a health care worker from the subject's medical records, and stored, such as in a server or on-demand data storage such as cloud storage.

In certain embodiments, the clinical information may be collected from data repositories, such as electronic health records ("EHR") databases, hospital records databases, other patient file databases, Internet databases, and the like. In certain other embodiments, information may be input into a data repository by the subject, such as through voice commands or keyboard entry. This information may include, for example, an identification code, a reference number, subject name, etc. Alternatively, information may be obtained through the use of surveys and questionnaires. It is also contemplated that a subject may access or input clinical information or information input to the system through biometric identification, facial recognition, retina scans, fingerprints, or even voice recognition including natural language processing.

Data repositories may be stored in one or more non-transitory data storage devices, such as, but not limited to, those described below with reference to FIG. 11A, FIG. 11B, and FIG. 11C. For purposes of this application, clinical information may include a summary of the subject's physical condition, symptoms, and health risk factor information. Symptoms may include an increase in abdominal girth, change in stooling pattern, signs of feeding intolerance, increase in oxygen requirements, an increase in apnea, low respiratory rate, and low heart rate. Clinical information may also include any other information relating to the subject's health, maternal information, and/or development. Maternal information may include the race, antibiotic exposure, and any other health information of the subject's mother prior to birth. Certain preferred embodiments permit the clinical information to be compared to national standards in order to place the subject's development in some additional context. In certain preferred embodiments, the clinical information is stored such that it may be readily retrieved from the server and/or input on a device by a user or caregiver. The clinical information may be modified as needed.

If the subject is identified as a premature infant in the earlier identification step, the gestational age of the subject is entered as the age of the subject.

When available, microbial sequence information may be prepared for the subject. A variety of microbial sequencing methods may be used, including shotgun metagenomics sequencing, targeted sequencing, rRNA sequencing, qPCR and microbial metatranscriptomics, or even an "at-home" self-administered test. The microbial sequence information may be loaded into the server. In certain preferred embodiments of the invention, the GM3 information may be revised based on the microbial sequence information. In certain other preferred embodiments of the invention, the GM3 information may be revised based on the metabolomics, wherein metabolism influences varying abilities to absorb/digest nutrients. As an example, if a preterm infant has an intrauterine growth restriction (e.g., resultant from insufficient placental nutrients), its metabolism may be permanently impaired.

In certain preferred embodiments of the invention, microbiome information of the subject may be developed through the collection of samples from the subject, such as biological samples of subject saliva, blood, tissue, stool, urine or any other biological material. The analysis of the samples and other information will permit the subject's microbiome profile to be determined and microbiome information developed. The microbiome information may be stored such that it may be readily retrieved from the server. In certain embodiments, the microbiome information will be stored with the clinical information.

In certain preferred embodiments, new clinical information corresponding to the subject's treatment, post menstrual age, gestational age, nutritional exposure, and the subject's antibiotic exposure may be identified and used to revise the GM3 information. It is contemplated also that the GM3 information may be revised based on a passage of time, for example, measured by days or hours of life.

In certain preferred embodiments of the invention, a gut maturity/readiness profile is calculated using all or a limited amount of microbiome, clinical and/or personal information. For example, a subject's mode of birth may be a factor for an infant. If the subject is not an infant, the mode of birth may or may not be taken into account as a factor when calculating the gut maturity/readiness profile. In another example, gestational age of a subject may be necessary only if the subject is a premature infant.

In certain preferred embodiments of the invention, a plurality of protocols may be prepared. For example, each gut maturity/readiness profile has an associated protocol. The protocols may be prepared based on changes in gut maturity or nutrition readiness, e.g., infant development, changes in clinical symptoms, changes in nutrition.

The plurality of protocols for the plurality of gut maturity/readiness profiles may be stored such that protocols may be readily retrieved from the system. For purposes of this application, a protocol may encompass plans, procedures, and rules for treating or supporting the subject. For example, a protocol may include rules and procedures applicable to the subject, such as, but not limited to, treatment procedures, nutritional plans, microbial interventions, and antibiotic exposure.

In certain preferred embodiments of the invention, a personalized microbiome health plan may be developed based on the gut maturity/readiness profile for subjects with symptoms of an unhealthy gut. At least one protocol corresponding to the gut maturity/readiness profile may be obtained from the system. The personalized microbiome health plan may include one or more dietary or nutritional strategies or introduction or withholding of antibiotics or other therapies.

In certain preferred embodiments of the invention, subject results are monitored in order to determine a subject's health status after execution of a protocol. For example, a patient's results may be monitored to determine the patient's response to the protocol—these responses may be, for example, in the form of changes to gut maturity profile or health status. In certain preferred embodiments, the system may process data associated with a subject result that has been input into the system and store the data in the server. Subject results may include protocols used, response to treatment, recovery time, nutritional information, metabolic measures, and microbiome information. The system may monitor the subject results to determine if a subject's health has improved after execution of a particular protocol. An improved subject status may be based on an analysis of the subject's microbiome, transcriptome or metabolome.

In certain preferred embodiments, the system may provide information regarding the effectiveness of a protocol. The system may analyze at least one protocol associated with the subject's health status. An effective protocol may include a protocol that is associated with a personalized microbiome health plan corresponding to an improved subject health state. In certain embodiments, the system may determine that a protocol is not effective and update the information regarding the effectiveness of the protocol to indicate that the protocol was not associated with a personalized microbiome health plan corresponding to an improved subject health state.

In certain preferred embodiments of the invention, the personalized microbiome health plan for the subject may be provided on a display of the system. Alternatively, the plan may be communicated via voice such as through a device with speech-generating capabilities. It is also contemplated that the plan can be made available in a form for aural or visual output, or both, e.g., a digital display and voice output. The device may obtain the gut maturity/readiness profile from the server in response to receiving a request for the same. The server may send the one or more protocols corresponding to the received gut maturity/readiness profile to the display or to a speech-generating device ("SGD") for voice output. In certain embodiments, the server of the system of the present invention may be any suitable server, and can include a network cloud server for storage and sharing of content across multiple systems.

While the invention is susceptible to various modifications and alternative forms, specific exemplary embodiments are shown by way of example in the following drawings which are described in detail. It should be understood, however, that there is no intent to limit the invention to the particular embodiments disclosed. On the contrary, the intention is to cover all modifications, equivalents, and alternatives falling within the scope of the invention as defined by the appended claims.

BRIEF DESCRIPTION OF THE DRAWINGS

FIG. 7 is a flow chart illustrating the steps of a certain preferred embodiment of a method of the present invention by which a plurality of protocols may be developed and made accessible for use in conjunction with a plurality of gut maturity/readiness profiles.

FIG. 10 illustrates a table of exemplary feeding recommendations based on gut maturity, stability (i.e. frequency of transitions among categories), and classification of gut community type.

DETAILED DESCRIPTION OF THE INVENTION

The present invention relates generally to a system and methods by which a microbiome-based action component may be developed that is useful to establish, restore, promote, and/or maintain subject health. More specifically, the system and methods of the present invention may be used to develop a microbiome-based action component that efficiently summarizes the state of a subject's microbiome and measures of gut maturity and development in case of infants and nutritional readiness in case of adults. Such an efficient summary may be used for a variety of reasons, for example, to render more immediate decision making such as health care to a subject or to render a nutritional plan for the subject. Certain specific embodiments of the present invention may be used to facilitate the development of a microbiome-based action component that provides, in addition to the efficient summary, a subject-specific, personalized microbiome health plan that includes options that may be followed in order that the subject may achieve personal health, growth, and development goals given the state of the subject's microbiome.

Figure 1:
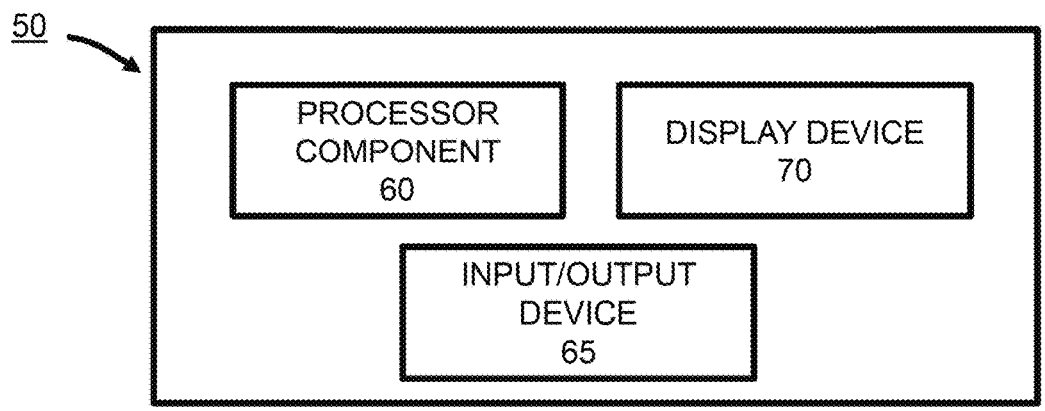
FIG. 1 is a block diagram illustrating a system that may be used to implement one or more methods of the invention.

In the drawings, where like numerals represent like components, FIG. 1 is a block diagram illustration of a system 50 according to one preferred embodiment of the invention. FIG. 1 includes at least a processor component 60 and a display device 70. The processor component 60 executes the instructions of the invention for developing a gut maturity/readiness profile of a subject and, through the use of that information, calculating all aspects of the gut maturity/readiness profile for the subject and other components described below.

In certain preferred embodiments of the present invention, the processor 60 may process the gut maturity/readiness profile and, with other information, develop a personalized microbiome health plan based on that profile for the subject. The system 50 may provide one or more default arrangements for displaying the gut maturity/readiness profile and/or the personalized microbiome health plan on the display device 70. For example, the system 50 may be configured to provide a display of the subject's gut maturity/readiness profile, the subject's personalized microbiome health plan, or both. The system 50 may also be configurable to revise all or parts of the gut maturity profile and/or personalized microbiome health plan in line with updated GM3 information.

A display device 70 can be used to communicate the gut maturity/readiness profile and/or personalized microbiome health plan in visual, audible, or tactile form, and may include, for example, a monitor, a speaker, or touch screen. The display device 70 may provide various types of additional content—such as an image, a moving picture, a text, music, a graphic user interface ("GUI"), an application execution screen, and the like—in addition to the gut maturity/readiness profile, personalized microbiome health plan, and/or nutrition plan. In certain preferred embodiments, the display device 70 may display a user interface screen that facilitates configuration of system 50 by a user including through the use of at least one selected from an input component such as a keypad, a touch pad, touch screen, a list menu, and an input window. The system 50 may further recognize interactions that may not involve touch. For example, the system 50 may include a variety of input/output devices 65. Input/output devices 65 may include any component for aural or visual input/output, for example, a camera, and/or microphone, to detect various inputs (e.g. user audio, user gestures, barcodes, etc.) or communicate various outputs (e.g., voice). Some examples of the display device 70 may be or may include a liquid crystal display ("LCD") panel, an organic light-emitting diode ("OLED"), and the like.

Figure 2A:
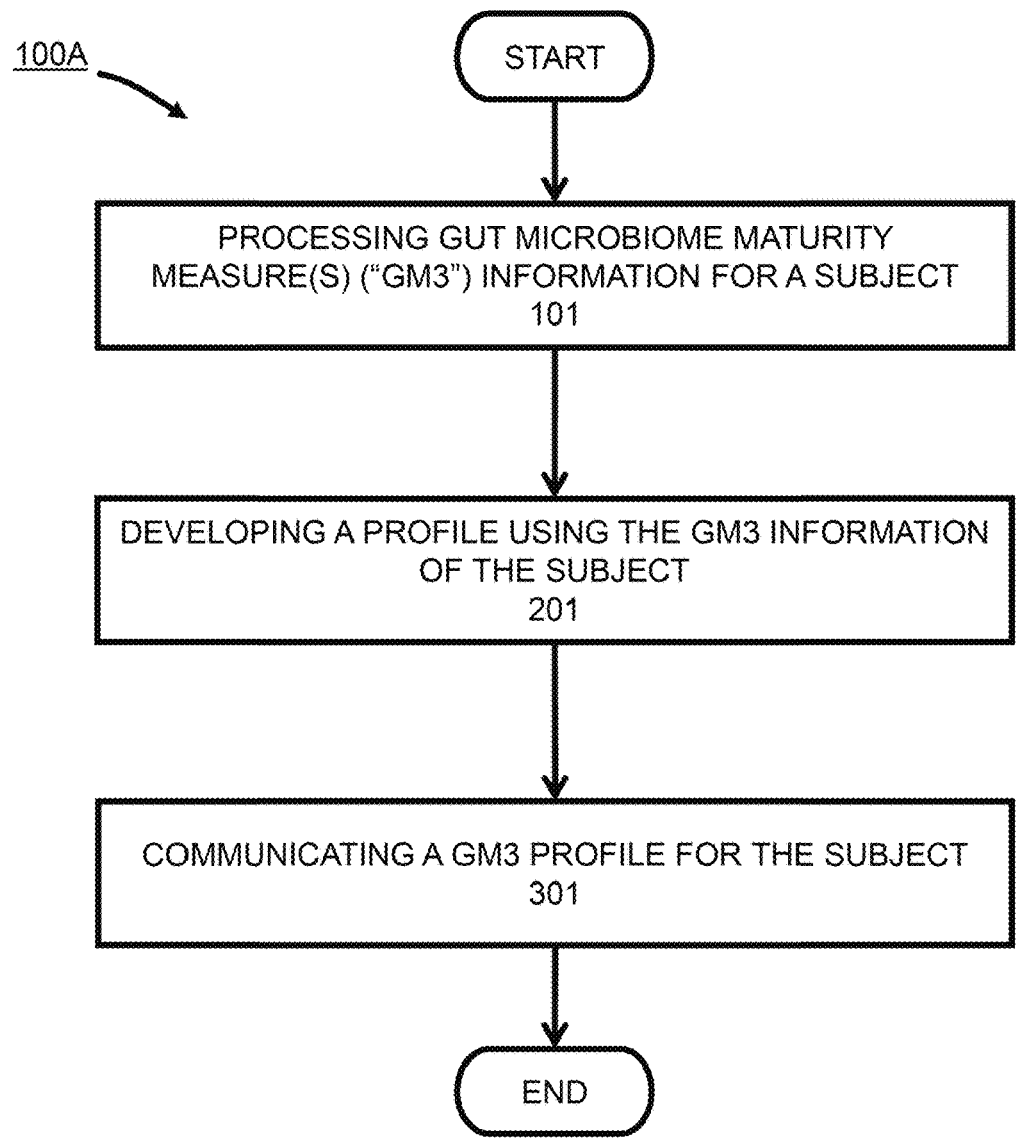
FIG. 2A is a flow chart illustrating the steps of one certain preferred embodiment of a method of the present invention by which one microbiome-based action component—a gut maturity/readiness profile—may be developed.

FIG. 2A is a flowchart 100A illustrating the steps of one certain preferred embodiment of a method according to the present invention by which one microbiome-based action component—the gut maturity/readiness profile—may be developed. The method of operation begins and, in step 101, the gut microbiome maturity measure(s) ("GM3") information of a subject is accessed. In step 201, a gut maturity/readiness profile is developed using the GM3 information of the subject. In step 301, the gut maturity/readiness profile and/or personalized plan for the subject is communicated, either aurally, visually, or both. For example, the profile may be displayed on display device 70 or communicated via voice through an input/output device 65.

Figure 2B:
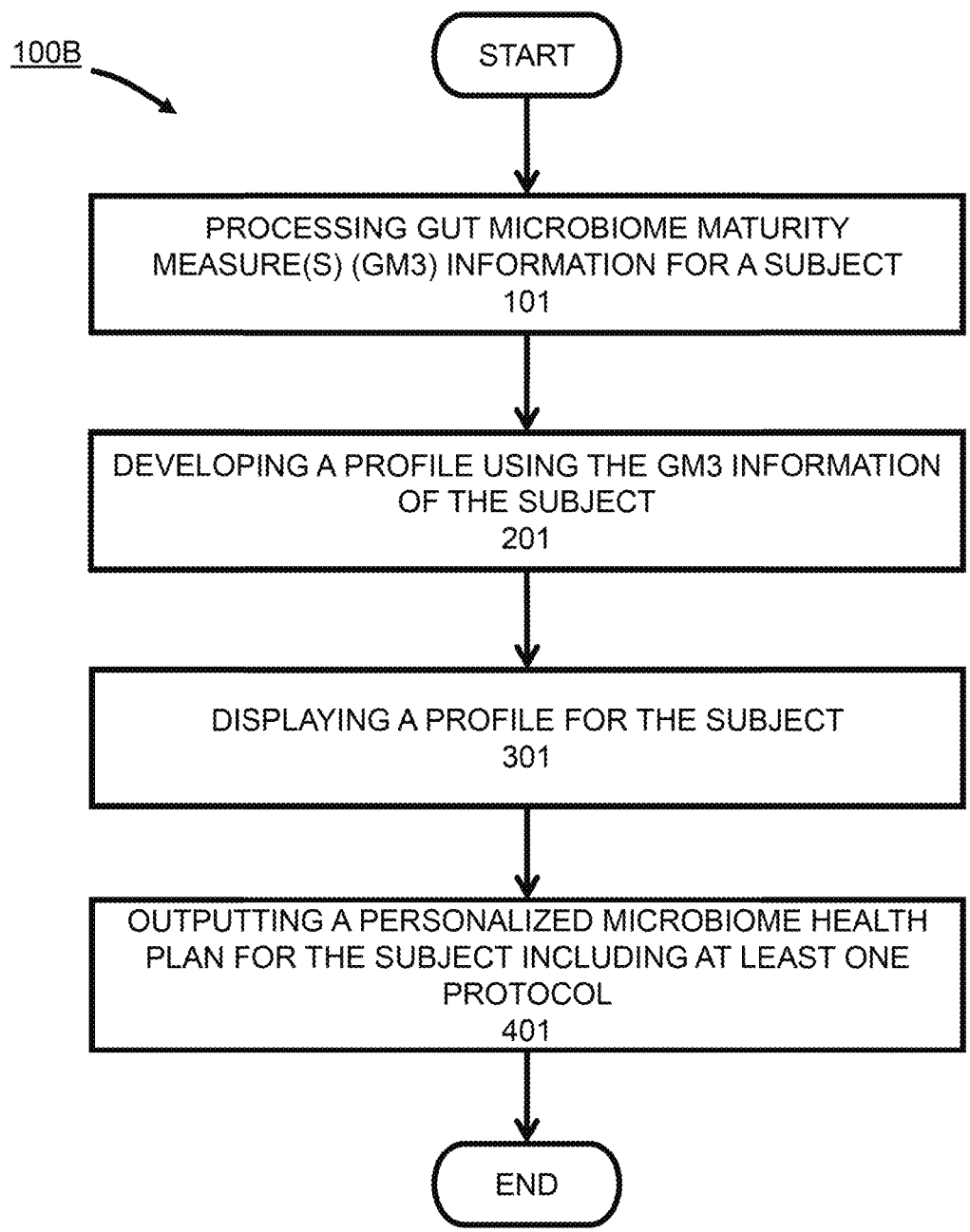
FIG. 2B is a flow chart illustrating the steps of another certain preferred embodiment of a method of the present invention by which an additional microbiome-based action component—a personalized microbiome health plan—may be developed.

FIG. 2B is a flow chart 100B illustrating the steps of another certain preferred embodiment of a method according to the present invention by which an additional microbiome-based action component—a personalized microbiome health plan or nutrition plan—may be developed based on the GM3 information, particularly the gut maturity/readiness profile. The certain embodiment illustrated in FIG. 2B provides the personalized microbiome health plan with at least one health protocol for the subject in step 401.

FIG. 3 through FIG. 7 illustrate flowcharts further detailing the exemplary operation of certain embodiments of the system 50 illustrated in FIG. 2A and FIG. 2B.

Figure 3:
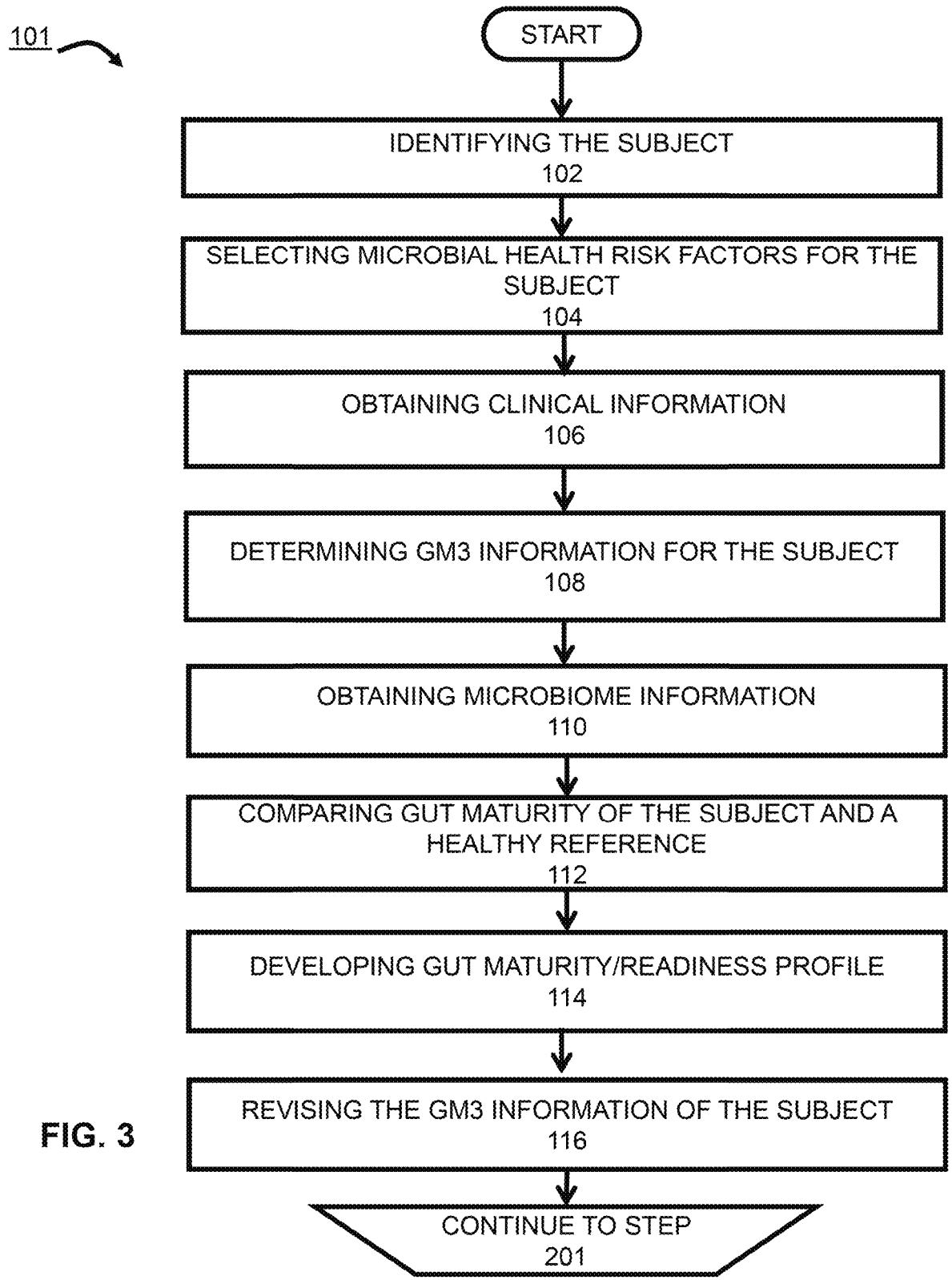
FIG. 3 is a flow chart illustrating the steps of a certain preferred embodiment of a method of the present invention by which the gut maturity/readiness information may be developed.

FIG. 3 is a flowchart 101 showing the steps of a certain preferred embodiment of a method according to the present invention by which the gut maturity/readiness profile may be developed for the operation of the embodiments of the systems identified as step 101 in FIG. 2A and FIG. 2B. After the operation begins, the subject is identified in step 102. The subject may be any mammal, but the examples discussed in this application make reference to humans. Once the subject is identified, in step 104, microbial health risk factors of the subject will be selected. Microbial health risk factors may include the subject's mode of birth (i.e. vaginal or cesarean section), perinatal risk factors such as maternal body mass index, age, exposure to antibiotics and the nutrition the subject is receiving or the subject's diet. If the subject is a preterm infant, the microbial health risk factors may include the gestational age of the subject at birth. Microbial health risk factors may be stored in any server accessible to the system 50.

In step 106 of the certain illustrated embodiment, clinical information, such as medications administered and diagnoses, of the subject is obtained. Clinical information may be stored in any server accessible to the system 50. The clinical information of a subject may be organized according to date, priority of condition, or other technique for organizing data. In step 108, measures of gut maturity/readiness are determined for the subject. In step 110, microbiome information of the subject is obtained. Microbiome information may include historic microbiome information, real-time-based microbiome information, derived microbiome information, predictive microbiome information, and combinations thereof.

In step 112, a comparison of the measures with a healthy reference is made. In step 114, gut maturity/readiness profile for the subject is developed advantageously from some or all information within a wide range of information that may include the personal or clinical information of the subject such as, but not limited to, the symptoms, microbial health factors, and other information of a subject, such as the subject's age (or in the case of a premature subject, adjusted gestational age), the symptoms, mode of birth, nutrition exposure, and antibiotic exposure.

In step 116, the GM3 information may be revised for the subject. In order to produce a microbiome-based action component, the operation continues to step 201 shown also in FIG. 2A and FIG. 2B.

Figure 4:
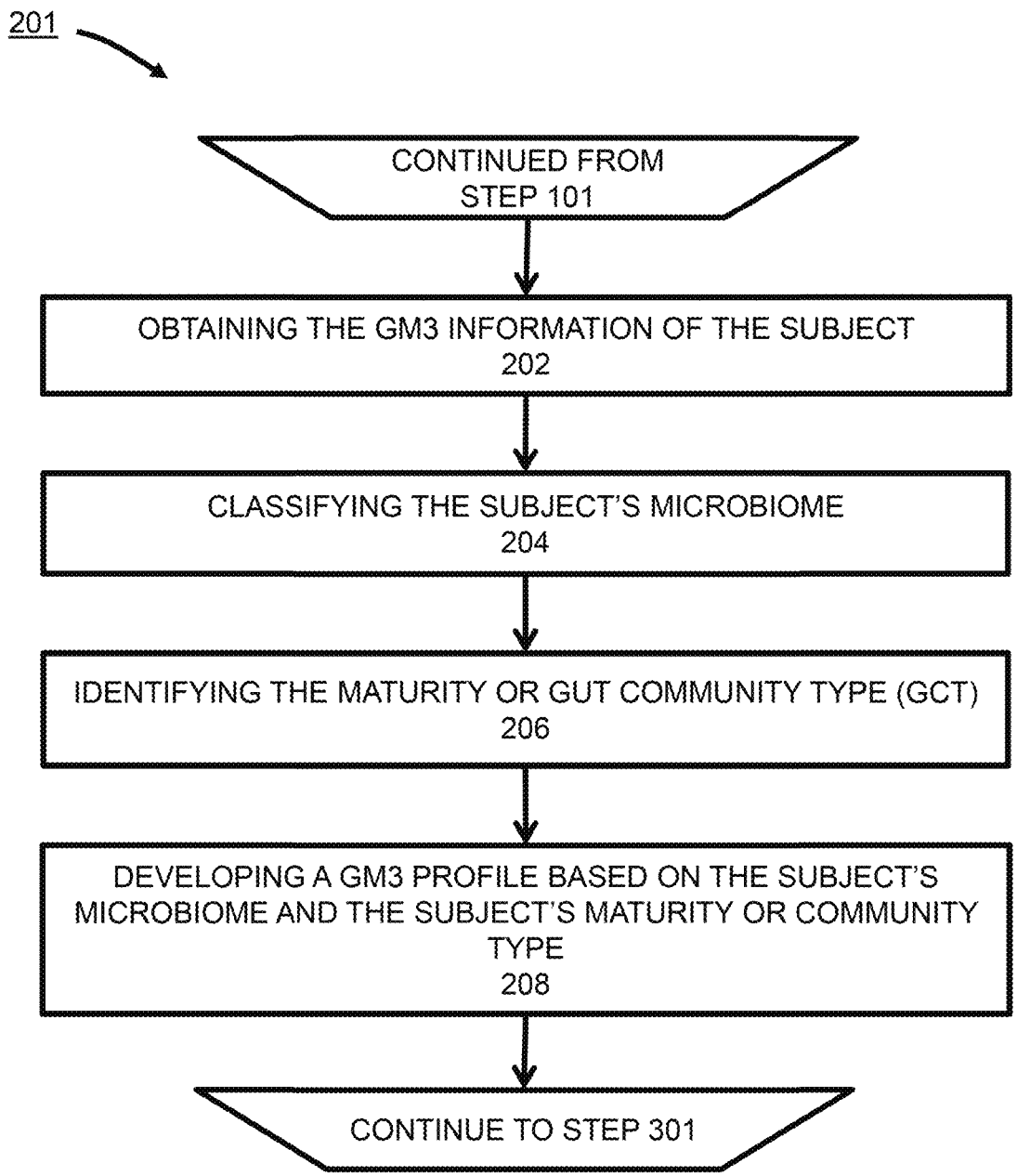
FIG. 4 is a flow chart illustrating the steps of a certain preferred embodiment of a method of the present invention by which a gut maturity/readiness profile may be developed from microbiome, clinical and personal information.

FIG. 4 is a flowchart 201 illustrating the steps of a certain embodiment of a method according to the present invention by which a certain microbiome-based action component—a gut maturity/readiness profile—may be developed from the microbiome, clinical and personal information. The operation is continued from step 101, one embodiment of which is shown in FIG. 3. In step 202, the measures contributing to the gut maturity/readiness profile developed for a subject are obtained. These measures may include the revised information developed in step 116 of FIG. 3. In step 204, the subject's microbiome is classified to a gut community type ("GCT"). The GCT, or stage, is a summary of the underlying complex microbiome community structure based on the relative abundance of species in all samples. In step 206, the gut maturity is identified for the subject. In step 208, a gut maturity/readiness profile will be developed for the subject based on the clinical, personal information and the microbiome of the subject.

If the development and output of an additional microbiome-based action component—personalized microbiome health plan—is desired, the operation will continue to step 401, shown in FIG. 2B, FIG. 5, FIG. 6A, and FIG. 6B.

Figure 5:
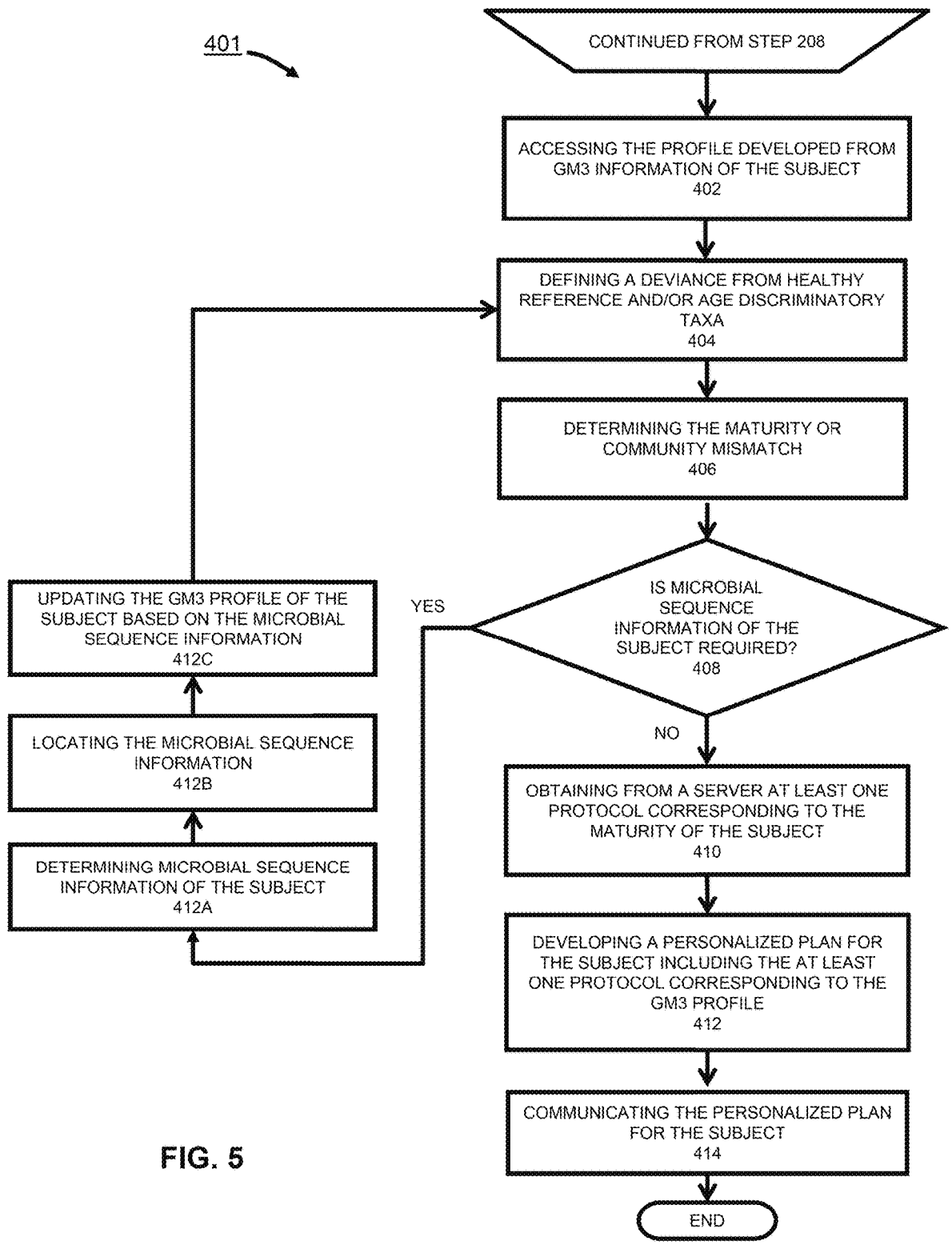
FIG. 5 is a flow chart illustrating the steps of a certain preferred embodiment of a method of the present invention by which a personalized microbiome health plan may be developed.

FIG. 5 is a flowchart 401 illustrating the steps of a certain preferred embodiment of a method according to the present invention by which a personalized microbiome health plan or nutrition plan may be developed. The operation is continued from step 208 shown also in FIG. 4. In step 402, a gut maturity/readiness profile of a subject—subject—is accessed. The system 50 may store a number of protocols that have been prepared for different GM3 values.

In step 404, a deviance from a healthy reference is defined or age discriminatory/age-specific taxa is defined. In step 406, a maturity or community mismatch is determined. For example, a mismatch occurs when the actual (gestational/chronological) age does not match the implied/calculated age, i.e., maturity level (inferred from the analysis).

In step 408, it will be determined whether microbial sequence information of the subject is required based on comparing the gut maturity measures threshold to a healthy reference. Microbial sequence information may include a subject's functional information and biological sequence/structure information, including without limitation genomic sequence information, mRNA sequence information, protein sequence information, and information on secondary and tertiary structures.

If microbial sequence information is not required, in step 410, at least one protocol corresponding to the gut maturity/readiness profile of the subject is obtained—such as from a database in the server. This protocol may include plans, procedures, and rules for the subject to follow. For example, a protocol may include recommendations and guidelines for the subject such as, exercise regimen, treatment procedures, nutritional plans, microbial interventions, and antibiotic regimen. A protocol may be one which a regulating authority, government agency, clinical trials or any other accepted method or organization in the health community develops. In certain preferred embodiments, one or more protocols may be generated by the system. Preferred embodiments of a protocol may also include suggested procedures that a healthcare professional, caretaker, or the subject may follow. For example, a protocol may include care components in which a caretaker may exercise discretion in attending to a subject, while another protocol may suggest that a caretaker follow an established sequence of actions. A protocol may also include rules and procedures that are specific to the training and certification of a caretaker. Further, a protocol may include sub-protocols that may be used in a comprehensive care plan. For example, a sub-protocol may be included that concerns the subject's nutrition and suggests certain feeding activities for the subject. Protocols may further suggest the degree to which specific treatment be administered. Specified schedules and timers for taking an action (e.g. administering a treatment) may also be included in a protocol.

In step 412, a personalized microbiome health plan may be developed for the subject that includes at least one protocol corresponding to the gut maturity/readiness profile. More than one protocol may exist for a particular gut maturity/readiness profile, and each protocol may include one or more sub-protocols corresponding to the gut maturity/readiness profile. The personalized microbiome health plan will be specific to the subject based on the measure of gut maturity/readiness, for example, through the use of the steps 201 shown in FIG. 4. Accordingly, the protocols will be tailored to the condition and gut maturity/readiness profile of the subject. In step 414, the personalized microbiome health plan for the subject is communicated on a display of a device or via voice.

If, at step 408, the microbial sequence information of the subject is required, in step 412A, the microbial sequence information of the subject will be determined. The microbial sequence information may be stored in the system 50 or in any server accessible to the system 50. In step 412B, the microbial sequence information will be located from the server. In step 412C, the GM3 value of the subject will be updated using the microbial sequence information and the process reverts back to step 404.

Figure 6A:
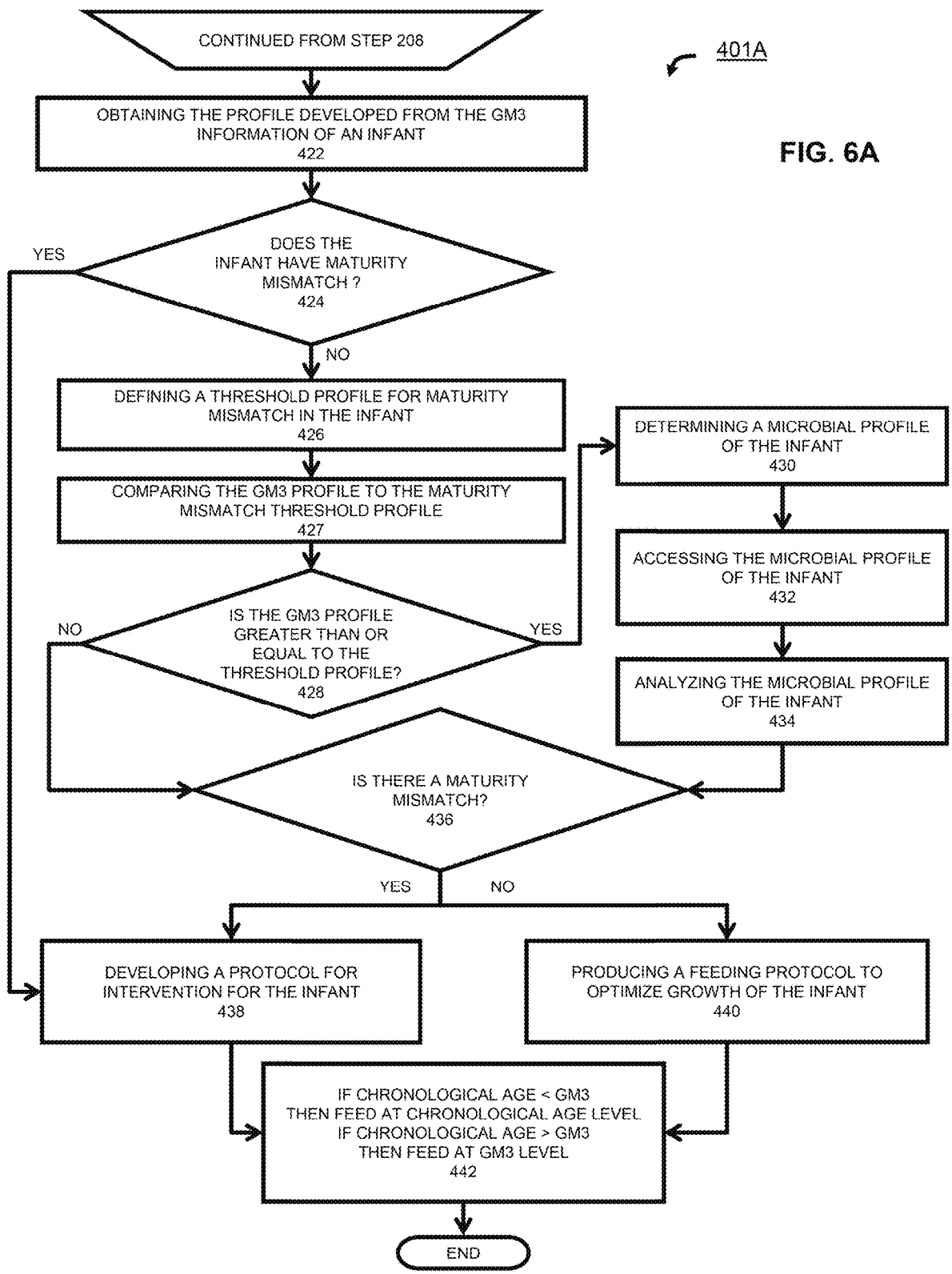
FIG. 6A a flow chart illustrating the steps of a certain preferred embodiment of the present invention by which a personalized microbial health plan may be developed and displayed for an infant.

FIG. 6A is a flowchart 401A illustrating the steps of a certain preferred embodiment according to the present invention by which for displaying a personalized microbial health plan, particularly for an infant in this example, may be developed and displayed. The operation is continued from step 208 shown in FIG. 4. In step 422, the gut maturity/readiness profile—for the subject—is obtained. In step 424 if the infant has a maturity mismatch, then a protocol for intervention may be developed at step 438. If the infant does not have a mismatch in step 424, then a threshold profile for maturity mismatch is defined in step 426. In step 427, it will be determined whether the profile of the subject is greater than the threshold profile by comparison.

If the subject's measures of gut maturity/readiness is greater than the threshold value at step 428, in step 430, a microbial profile for the subject will be determined. A microbial profile may include taxonomic and/or phylogenetic identification of the microbes in a biological community. A microbial profile can also include quantitative information about one or more microorganisms that have been identified in the microbial community. Microbial profiles may be in various forms, such as a list, graph, table, or any other appropriate representation of microorganisms in a community. Taxa—age discriminatory or age-specific—are evaluated to determine which taxa play a role. A microbial profile can include a set of species that are correlated to the GM3 information. A microbial profile may be used for identifying pathogenic and nonpathogenic microbial organisms in biological and non-biological samples. A microbial profile may be determined using any of a number of methods. For example, microbes in a biological sample can be genetically sequenced or determined via qPCR and colonies identified. Once the microbial profile of the infant is determined, in step 432, the microbial profile of the subject is accessed. In step 434, the microbial profile of the subject is analyzed.

If the measures of gut maturity/readiness is less than the threshold value at step 428 or, once the microbial profile of the subject is analyzed at step 434, in step 436, it will be determined what the developmental state or maturity level of the gut. If there is a mismatch at step 436, a protocol for early intervention will be developed for the subject in step 438. An early intervention protocol may include administration of a microbial agent, intravenous, enteral or oral nutrition, and/or intravenous hydration. In certain embodiments, the microbial agents may be one or more prebiotic or probiotic formulations. If at step 436, there is alignment of age of gut maturity and actual (chronological) age, a feeding protocol to maximize growth, maintain, or optimize health will be produced for the subject in step 440. A feeding protocol may include a change in diet and/or a change in the rate of the feeding. For example, if there is not a high risk of disease for the subject, there may be an increase in the feeding rate for the subject. In step 442, a personalized microbiome health plan will be formulated for the infant subject. The plan is determined with respect to chronological age. If chronological age is less than GM3, then the recommendation is to feed at the chronological age level for the subject. If the chronological age is greater than GM3, then the recommendation is to feed at the GM3 level for the subject. The personalized microbiome health plan for the subject may be communicated such as via voice or displayed on a display of a device.

Figure 6B:
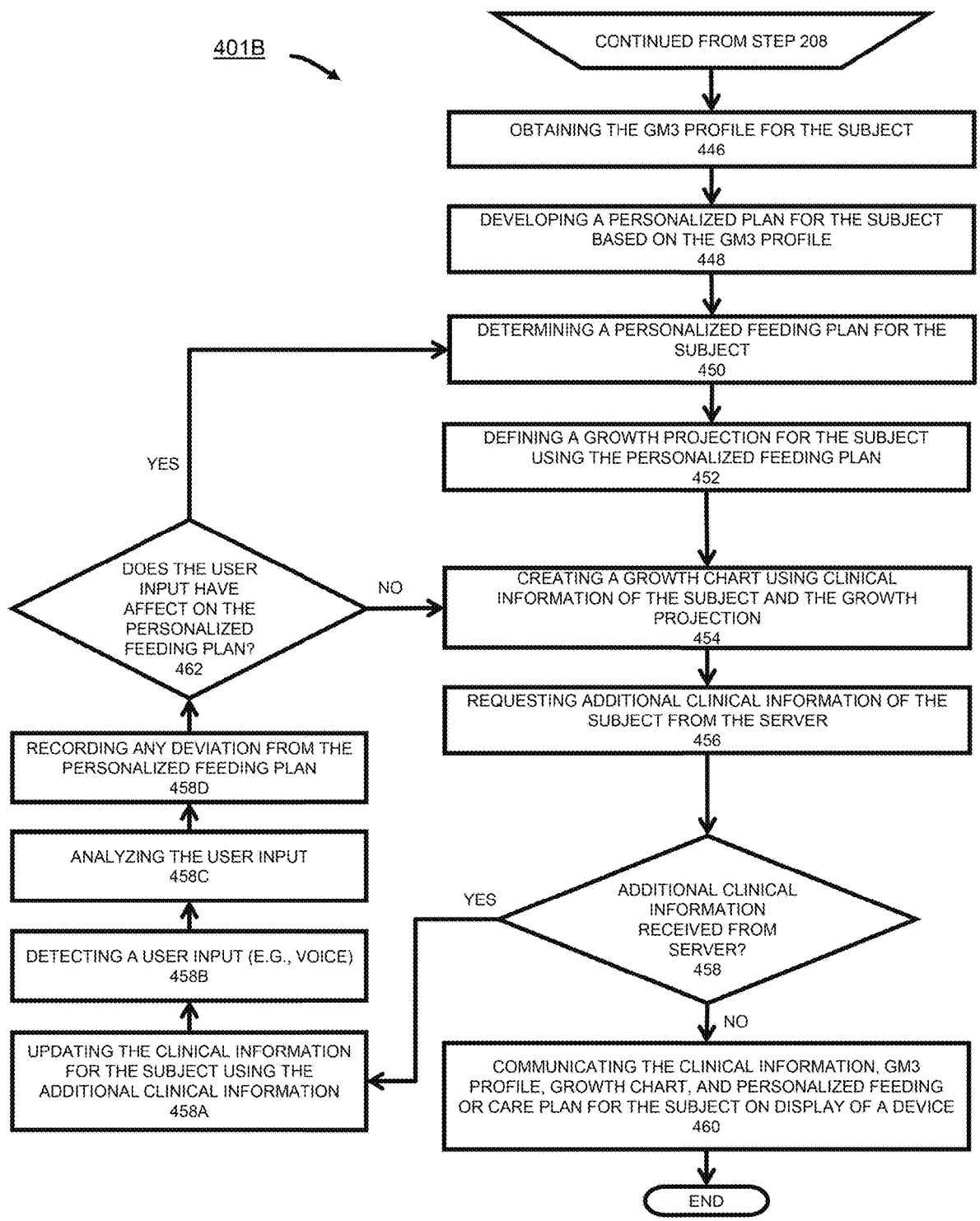
FIG. 6B is a flow chart illustrating the steps of a certain preferred embodiment of a method of the present invention by which a personalized microbial health plan may be developed based on new clinical and other information and displayed.

FIG. 6B is a flowchart 401B providing more detail of step 301 of FIG. 2, in accordance with an embodiment of the system 50. The operation is continued from step 208. In step 446, the gut maturity/readiness profile for the subject is obtained. In step 448, a personalized microbiome health plan is developed for the subject based on the gut maturity/readiness profile. In step 450, a personalized feeding plan is determined for the subject. In step 452, growth is projected based on the personalized feeding plan. In step 454, a visual growth chart of the projection for the subject is created using the personalized feeding plan. In certain embodiments, system 50 may include a growth module to generate a growth projection. The growth projection may be defined using a number of variables associated with the feeding plan. For example, the type of nutrition, the amount of nutrition, and the frequency of feeding may be used to project growth.

In step 456, additional clinical information of the subject is requested from the server. In step 458, the system 50 will determine whether additional information was received from the server. If no additional information is received at step 458, the microbial health risk factor information, gut maturity/readiness profile, growth chart, immaturity mismatch and personalized feeding plan may be displayed on a display or communicated via voice through a speaker of a device in step 460.

If, at step 458, the system 50 determines that the additional clinical information was received from the server, in step 458A, the system 50 may update the gut maturity/readiness profile for the subject using the additional clinical information. The additional information may be input verbally or by a device that is configured by a user. In step 458B, the system 50 will detect the user input. In step 458C, the system 50 will analyze the user input. In step 458D, the system will record any deviation by the user from the personalized feeding plan. In step 462, the system 50 will determine whether the user input has an effect on the personalized feeding plan. If the user input does have an effect on the personalized feeding plan at step 462, the operation reverts back to step 450. If the user input does not have an effect on the personalized feeding plan at step 462, the operation will proceed to step 454.

FIG. 7 is a flowchart 470 illustrating the steps of a certain preferred embodiment according to the present invention by which a plurality of protocols may be developed and made accessible for use in conjunction with a plurality of microbiome values. The method begins in step 472, a plurality of protocols is prepared for a plurality of gut maturity/readiness profiles. In step 474, the plurality of protocols for the plurality of gut maturity/readiness profiles is stored in a server. In step 476, protocol status information is maintained on a server for the plurality of protocols. The protocol status information may include information indicating whether a protocol was effective for a corresponding gut maturity/readiness profile. An effective protocol may include a protocol that corresponds to a personalized microbiome health plan, which has been previously administered to a subject and provided successful results (i.e. the subject has shown signs of recovery and/or healthy development). In step 478, the server will request a gut maturity/readiness profile from a device and in step 480 the server will receive a gut maturity/readiness profile from the device. In step 482, at least one protocol corresponding to the received gut maturity/readiness profile will be determined. In step 484, at least one protocol will be analyzed. The protocol may be analyzed based on a number of factors. For example, the protocol may be analyzed based on a healthy subject result that has been associated with the protocol. In another example, the protocol may be analyzed based on new clinical information, (development of new) nutritional or microbial options, literature, and/or case studies. In step 486, the server will determine if a protocol is effective. If the protocol is effective at step 486, in step 488, a personalized microbiome health plan will be developed including protocols corresponding to the gut maturity/readiness profile. The personalized microbiome health plan may include only effective protocols or may include all protocols corresponding to the gut maturity/readiness profile with indicators for protocols that are not effective. In step 490, the personalized plan will be sent to the device for display or communicated using a speech-generating device. If at step 486, a protocol is not effective, in step 486A, protocol information status in the database will be updated to indicate that the protocol is not effective. The operation will revert back to step 476.

Figure 8:
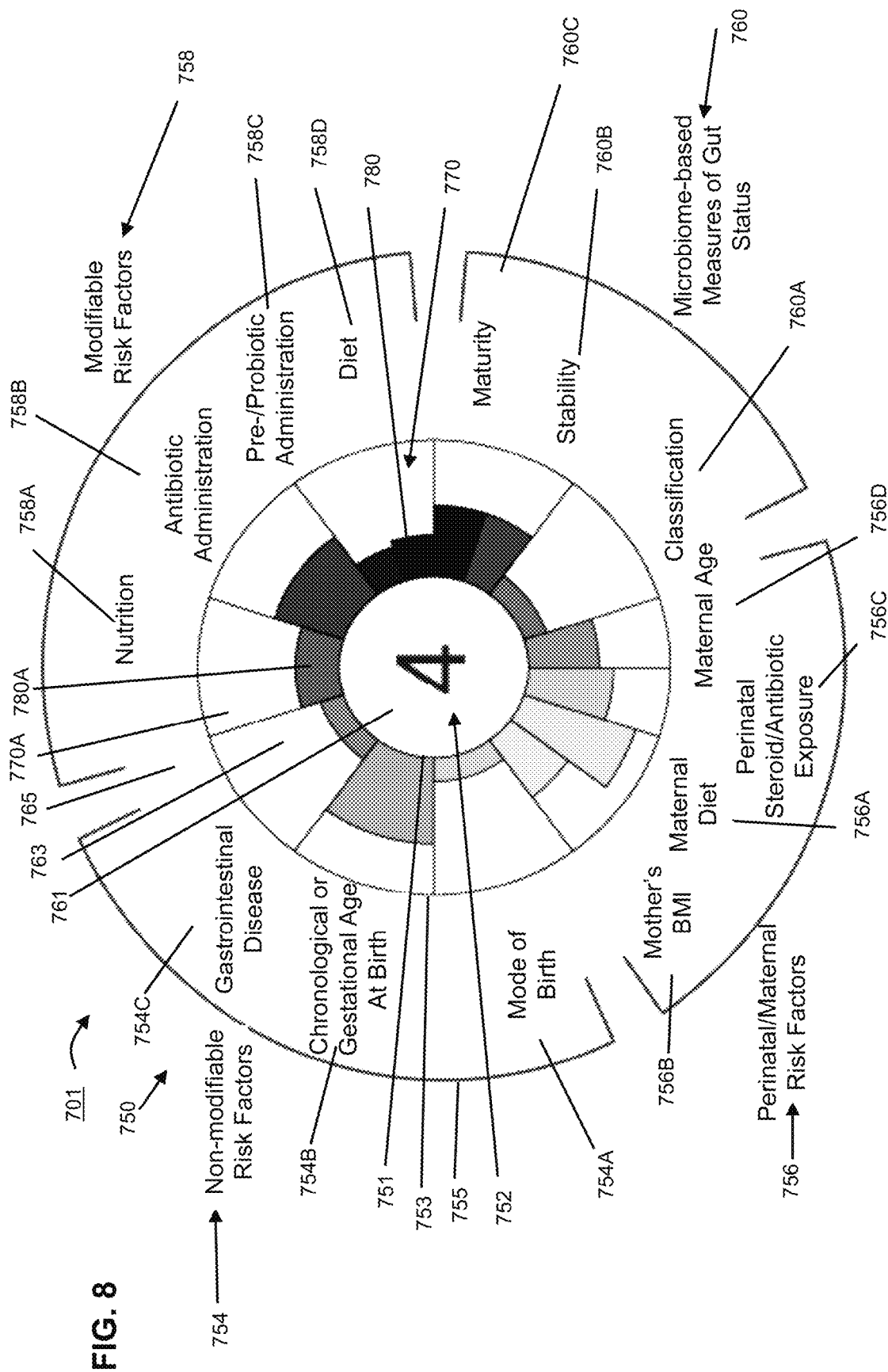
FIG. 8 illustrates a display of information developed according to the present invention and that may be provided to a user. Display includes both clinical and microbiome information, including non-modifiable and modifiable data, in a text and graphical format.
Figure 9A:
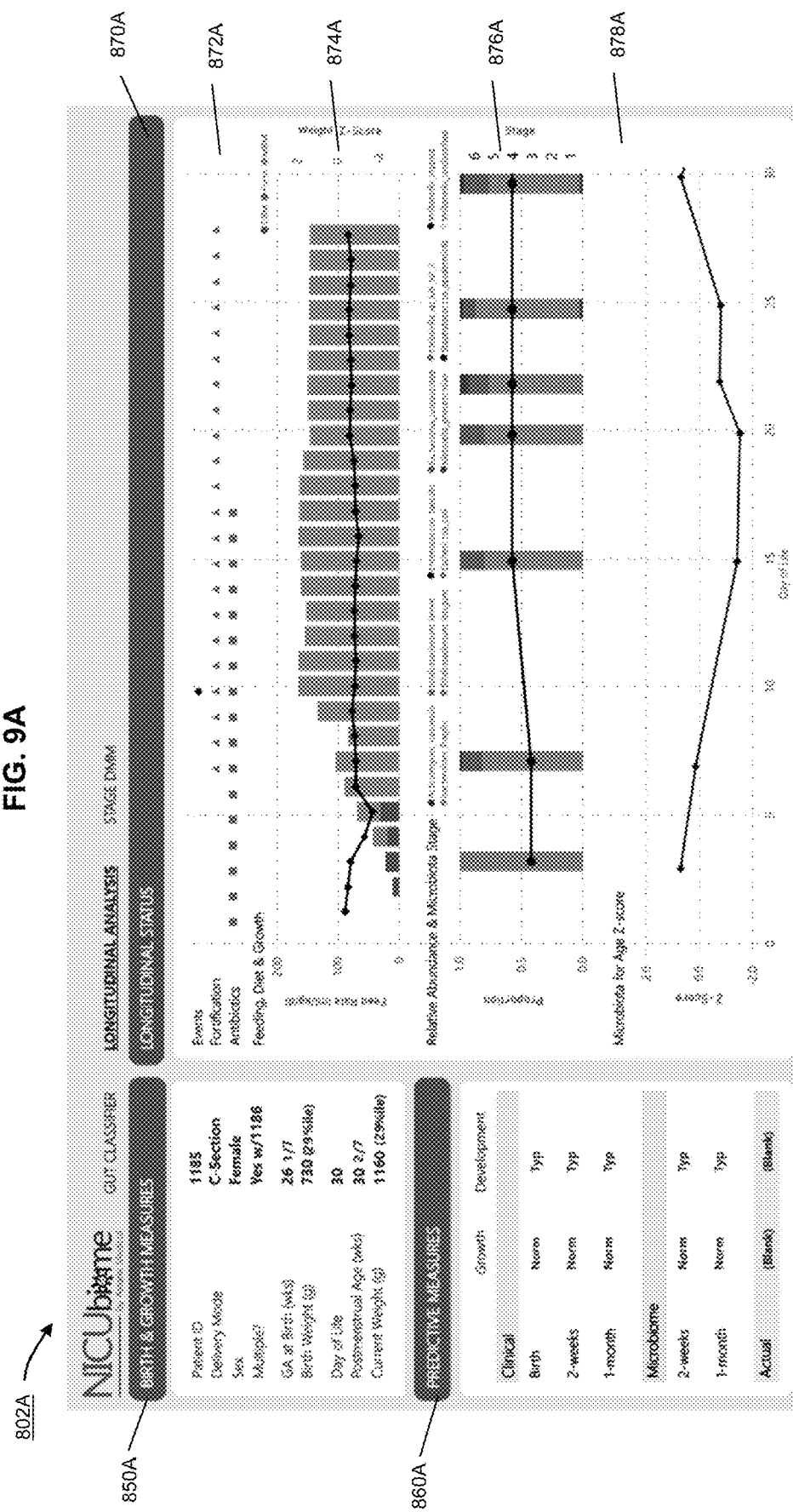
FIG. 9A illustrates a display of information developed according to the present invention and that may be provided to a user. Display includes both clinical and microbiome information, including non-modifiable and modifiable data, with emphasis on graphical representation. Snapshot of first month of stay.
Figure 9B:
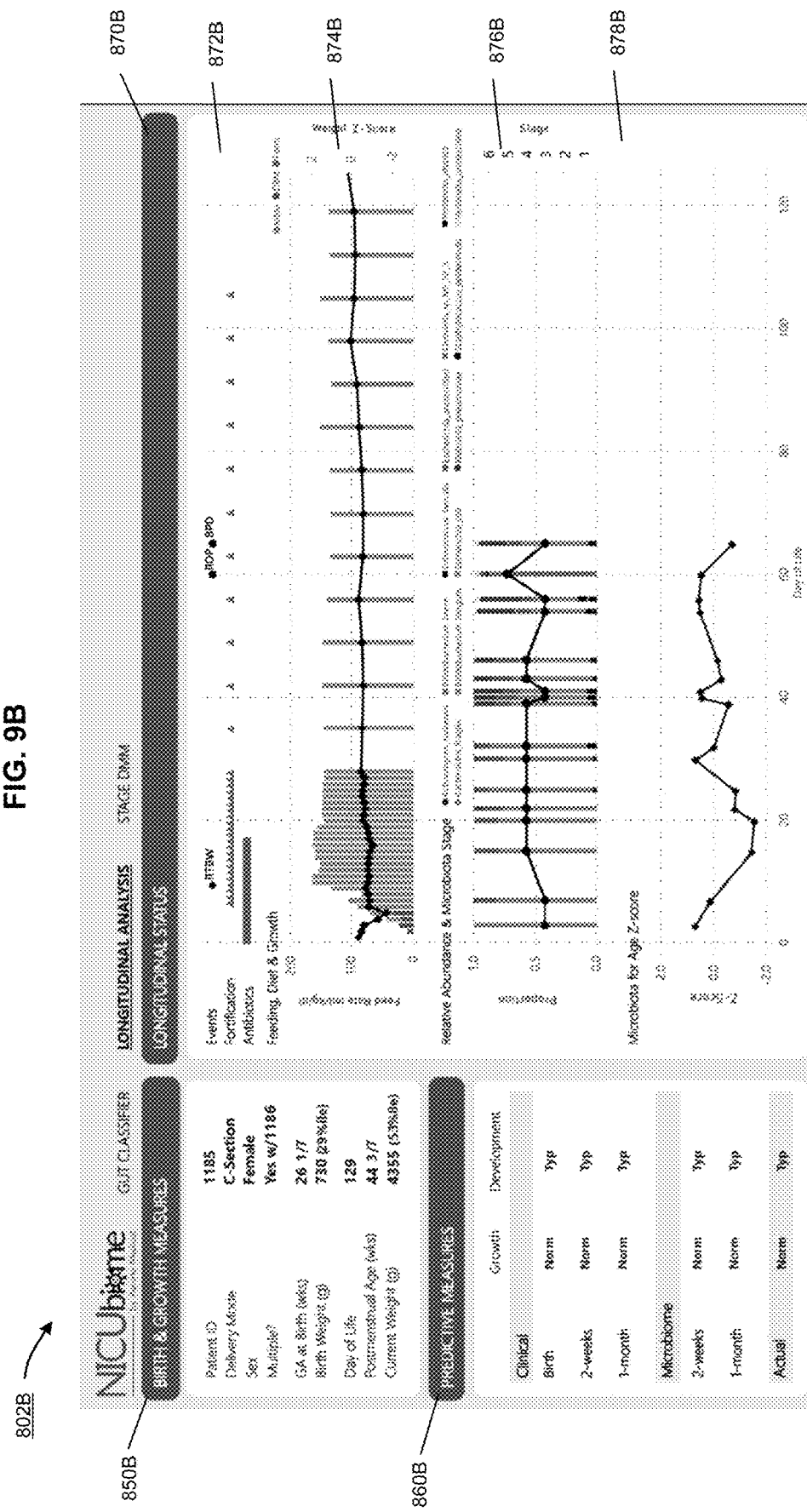
FIG. 9B illustrates a display of information developed according to the present invention and that may be provided to a user. Display includes both clinical and microbiome information, including non-modifiable and modifiable data, with emphasis on graphical representation. Snapshot of full neonatal intensive care unit ("NICU") stay.

FIG. 8 shows one preferred embodiment of a display of the gut maturity/readiness profile. FIG. 9A and FIG. 9B show other preferred embodiments of a display of the gut maturity/readiness profile. The gut maturity/readiness profile may be represented through a variety of means, including a numerical value, an alphabet, letter, or word value, a symbol, or a combination of two or more such representations.

FIG. 8 is an image illustrating a certain preferred embodiment of another display of information developed according to the present invention that may be provided to a user. In FIG. 8, an exemplary dashboard display 701 is shown that provides an exemplary GM3 value 752, in accordance with an embodiment of the invention. Exemplary dashboard display 701 may be provided on a display device. Exemplary dashboard display 701 provides the GM3 value view 752 for a subject, the non-modifiable risk factors for the subject 754, the modifiable risk factors 758, the perinatal risk factors 756, measures of gut maturity 760, including metabolic capacity and the associated weighting of each element 770 in calculation of the GM3 value. Additional detailed information may be shown in response to a user selecting the "Risk Factors" option 754, 756, and 758, which will provide additional information regarding the various microbial health risk factors used in calculating the GM3 value. Within the illustrated embodiment of the GM3 value view 752, Non-modifiable Risk Factors 754 is broken down into the following information components: "Mode of Birth" 754A, "Chronological Age or Gestational Age At Birth" 754B, and "GI Disease" 754C. In the illustrated embodiment, Perinatal Risk Factors 756 is broken down into the following information components: "Maternal Diet" 756A, "Mother's Body Mass Index ("BMI")" 756B, "Perinatal Steroid/Antibiotic Exposure" 756C, and "Maternal Age" 756D. In this illustrated embodiment, Modifiable Risk Factors 758 which is broken information components into "Nutrition" 758A, "Antibiotic Administration" 758B, "Pre-/Probiotics Administration" 758C, and "Diet" 758D. Within the dashboard display 701, "Microbiome-based Measures of Gut Status" 760 may be broken down to information components such as the illustrated "Classification" 760A, "Stability" 760B, and "Maturity" 760C as exemplary molecular markers of the state of the gut. In the illustrated process, the microbial health risk factors are weighted 770 to show each element's impact on the calculation of the GM3 value 752. One embodiment by which a GM3 value may be produced is the following:

$$f_1 w_1 + f_2 w_2 + f_3 w_3 + \ldots = \text{GM3 value}$$

in which the "f" factors are the microbial health risk factors and the "w" factors are the weightings corresponding to that factor's impact on the state of health as determined by the System. The sum of the individual factors multiplied by each corresponding weighting is totaled to provide the GM3 value.

As shown in FIG. 8, the dashboard display 701 comprises a graphical user interface 750 summarizing a state of the subject's microbiome and clinical and personal information. The graphical user interface 750 comprises concentric circles 751, 753, 755 forming a center circle 761, a first annulus 763, and a second annulus 765. The center circle 761 includes the calculated subject GM3 value 752. The first annulus 763 includes a plurality of pie chart elements 770, and the second annulus 765 identifies the factors—information. Each factor—754A, 754B, 756A, 756C, etc.—corresponds to a pie chart element 770 of the first annulus 763. And a size of each pie chart element 770 is representative of the weight value of the corresponding factor—754A, 754B, 756A, 756C, etc.—on the GM3 value. Each pie chart element 770 further includes a bar chart element 780. The length of the bar chart element 780 is representative of an impact of the factor on the calculated subject GM3 value.

For example, a "Nutrition" 758A factor of the Modifiable Risk Factor Category 758 corresponds to pie chart element 770A with bar chart element 780A. As seen, the size of the pie chart element 770A is greater than the size of the pie chart element for "Perinatal Steroid/Antibiotic Exposure" 756C and the length of the bar chart element 780A is less than the bar chart element for "Perinatal Steroid/Antibiotic Exposure" 756C. Therefore, while "Nutrition" 758A has a greater weight value than "Perinatal Steroid/Antibiotic Exposure" 756C on the GM3 value, "Nutrition" 758A nevertheless has less of an overall impact than "Perinatal Steroid/Antibiotic Exposure" 756C on the calculated GM3 value for the subject because the "Nutrition" 758A factor is less than the "Perinatal Steroid/Antibiotic Exposure" 756C factor.

A user can interrogate any element of the calculation to see its native value or state as well as its weighting factor for calculating the GM3 value.

FIG. 9A and FIG. 9B illustrate a display of information developed according to the present invention and that may be provided to a user. These displays are exemplary embodiments and are described in reference to an infant, but any mammal is contemplated such as an adult. The displays communicate profile information in the form of text, numbers, and graphs or charts.

In FIG. 9A, the exemplary dashboard display 802A provides a longitudinal analysis view. The illustrated embodiment of infant longitudinal analysis view includes "Birth and Growth Measures" 850A, "Predictive Measures" 860A, and "Longitudinal Status" 870A. Depending on the subject, the "Birth and Growth Measures" 850A provides identifying information for the subject such as delivery mode, sex, weight, etc. "Predictive Measures" 860A communicates the risk predictions of growth failure and non-typical development based on applying artificial intelligence/machine learning algorithms on clinical and/or microbiome data, at different time periods as well as actual growth and development.

The "Longitudinal Status" 870A provides a combined chart comprising a plurality of graphs to communicate occurrences such as "Events, Fortification, Antibiotics" 872A, "Feeding, Diet & Growth" 874A, "Relative Abundance and Microbiota Stage" 876A, and "Microbiota for Age Z-Score" 878A. The combined chart includes an x-axis directed to a number representing the "day of life" for the subject. All occurrences are illustrated on the combined chart according to the "day of life" on which it occurred. For the dual-axis graph communicating "Feeding, Diet & Growth" 874A, a first y-axis represents a "feed rate value" (ml/kg/d) and the second y-axis represents a "weighted Z-score". For the dual-axis graph communicating "Relative Abundance and Microbiota Stage" 876A, a first y-axis represents "proportion" and the second y-axis represents a "stage", which is the gut community type. For the graph communicating "Microbiota for Age Z-Score" 878A, the y-axis represents a "Z-score". Graphs of the plurality may be any type of graph, for example, control chart, run chart, strip chart, line chart, histogram, bar chart, stacked bar chart, scatterplot, etc.

In FIG. 9B, the exemplary dashboard display 802B provides a longitudinal analysis view extending over a longer period of time. As shown in the charts for "Events, Fortification, Antibiotics" 872A, 872B, icons such as circles, diamonds, squares, triangles represent one or more nutritional milestones, diagnoses, treatments, or occurrences such as: return to birthweight ("RTBW"), Retinopathy of prematurity ("ROP"), Bronchopulmonary dysplasia ("BPD"). Events may contain, but are not limited to solely these.

The graph "Feeding, Diet & Growth" 874A comprises a bar chart and a line chart. The bar chart indicates the feed rate for mother's breast milk ("MBM"), donor's breast milk ("DBM"), or formula ("FORM") at each day of life. A line chart represents the weighted z-score that describes a feed rate compared to a mean for a group of feed rate values.

The graph "Relative Abundance and Microbiota Stage" 876A comprises a bar chart and a line chart. Each type of microbiota—e.g., *Actinomyces turicensis, Bacteroides fragilis, Bifidobacterium breve, Escherichia coli, Veillonella atypica*, etc.—is identified by its own color or pattern. The bar chart comprises a plurality of bars with each bar comprising one or more colored portions. Each colored portion indicates the type of microbiota and the size of the portion indicates the amount of that microbiota with respect to other microbiota, the relative abundance, at a day of life of the subject. A line chart represents the gut community type ("GCT") of the subject at the day of life. The GCT is a summary of the underlying complex microbiome community structure based on the relative abundance of species in all samples. According to certain embodiments, stages may be identified by values, for example, developmental stages are identified by values 1 and 2, transitional stages are identified by values 3 and 4, and stable stages are identified by values 5 and 6 as shown on the second y-axis of the graph "Relative Abundance and Microbiota Stage" 876A.

The graph "Microbiota for Age Z-Score" 878A comprises a line chart representing the z-score that describes microbiota for the age of the subject with respect to a mean for a group of 'healthy' subjects at the same age and at the same day of life.

A health based on Microbiota for Age Z-score ("MAZ"), a temporal classification using DMM reflecting the underlying microbiome community structure based on taxa, and a tracking of transitions among classifications provides recommendations incorporating the various measures of gut status, including maturity, classification and stability. MAZ is a quantitative measurement that allows comparison of an infant's gut development or maturation against its chronological age, relative to healthy infants of similar chronological age. A temporal classification is defined as "stages" or gut community types ("GCT"), which is a summary of the underlying complex microbiome community structure based on the relative abundance of species in all samples (e.g., a population).

An example of the recommendations based on these individual measures is shown in FIG. 10. It is contemplated that once a recommendation or other health plan is implemented, a reassessment of the gut status metrics are evaluated, and new health plan recommendations are generated.

Figure 11A:
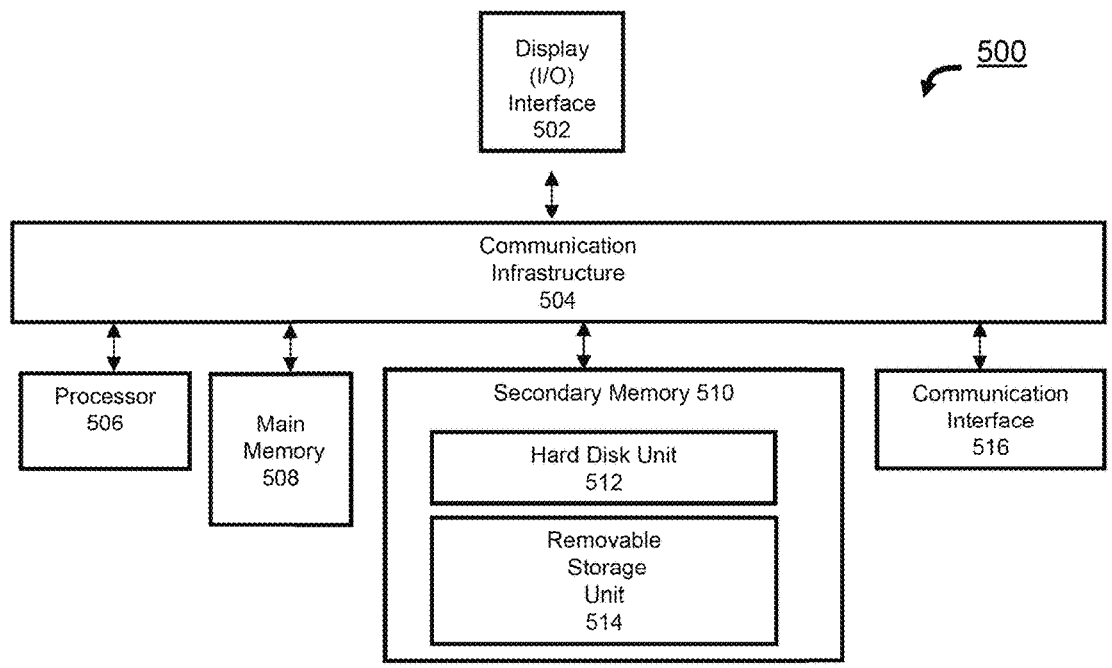
FIG. 11A is an exemplary computing system that may be used for implementation of all or a portion of the invention.

FIG. 11A illustrates an exemplary computer system 500 that may be used to implement the methods according to the present invention. One or more computer systems 500 may carry out the present invention according to processing instructions, or computer code.

Computer system 500 includes an input/output display interface 502 connected to communication infrastructure 504—such as a bus—which forwards data such as graphics, text, and information, from the communication infrastructure 504 to other components of the computer system 500. The input/output display interface 502 may be the display device 70 (FIG. 1) or, alternatively, a speaker, touchscreen, speech-generating device, printer, any other computer peripheral device, or any combination thereof, capable of communicating an area of interest. Furthermore, the interface 502 may be a keyboard, joystick, trackball, and mouse for the user to enter what he or she believes to be an area of interest.

One or more processors components 506 such as processor component 60 (FIG. 1) may be a special purpose or a general-purpose digital signal processor that processes certain information. Computer system 500 may also include a main memory 508, for example random access memory ("RAM"), read-only memory ("ROM"), mass storage device, or any combination of tangible, non-transitory memory as well as a secondary memory 510 such as a hard disk unit 512, a removable storage unit 514, or any combination of tangible, non-transitory memory. It is also contemplated that the memory may be portable storage device.

Computer system 500 may also include a communication interface 516, for example, a modem, a network interface (such as an Ethernet card or Ethernet cable), a communication port, a PCMCIA slot and card, wired or wireless systems (such as Wi-Fi®, Bluetooth®, Infrared), local area networks, wide area networks, intranets, etc. Communication interface 516 allows software, instructions and data to be transferred between the computer system 500 and external devices or external networks.

Computer programs, when executed, enable the computer system 500, particularly the processor 506, to implement the methods of the invention according to computer software instructions. The computer system 500 of FIG. 11A is provided only for purposes of illustration, such that the invention is not limited to this specific embodiment. It is appreciated that a person skilled in the relevant art knows how to program and implement the invention using any computer system.

The computer system 500 may be a handheld device and include any small-sized computer device including, for example, a personal digital assistant ("PDA"), smart handheld computing device, cellular telephone, or a laptop or netbook computer, hand held console or MP3 player, tablet, or similar hand held computer device, such as an iPad®, iPad Touch® or iPhone®.

Figure 11B:
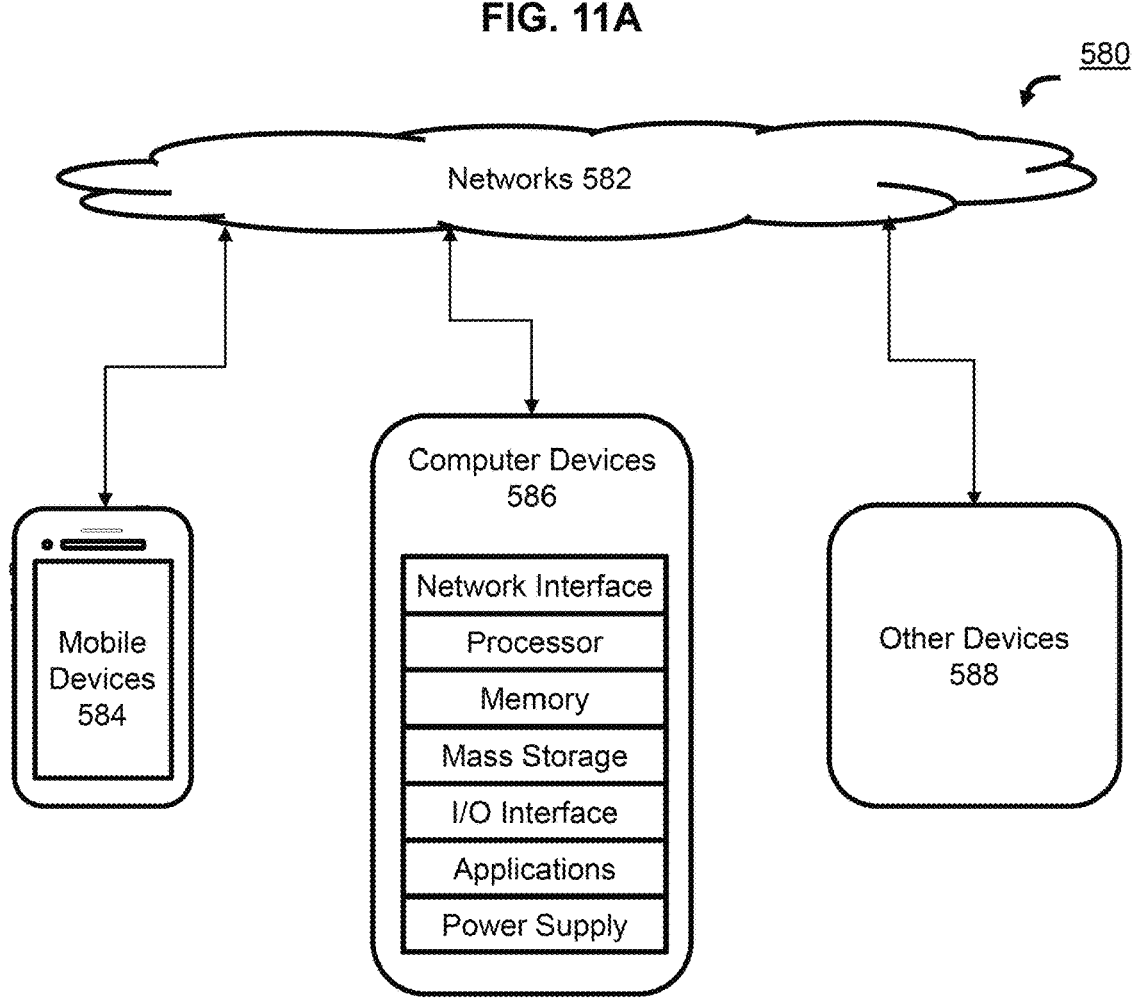
FIG. 11B is yet another exemplary computing system that may be used to implement all or a portion of the invention.

FIG. 11B illustrates another exemplary computing system 580 that may be used to implement all or a portion of the invention. As shown in FIG. 11B, a computer device 586, mobile device 584 and other devices 588 communicate via network 582. These embodiments permit the exchange of information between two or more devices, and enable synchronization of the output received, e.g., between a mobile device 584 and a computer device 586. The computing device 586 can include any device capable of communicating with other devices through a network 585. The computing device 586 can include a processor and memory, and may be an electronic tablet device, a personal computer, workstation, server, portable computer, mobile device, personal digital assistant, laptop, smart phone, WAP phone, an interactive television, video display terminals, gaming consoles, and portable electronic devices or any combination of these. The network 582 can include any network capable of carrying data, including the Internet, Ethernet, local area network, wide area network, and others, including any combination of these, capable of interfacing with, and enabling communication.

The computing device 586 can include any device capable of communicating with other devices through a network 585. The computing device 586 can include a processor and memory, and may be an electronic tablet device, a personal computer, workstation, server, portable computer, mobile device, personal digital assistant, laptop, smart phone, WAP phone, an interactive television, video display terminals, gaming consoles, and portable electronic devices or any combination of these. The network 582 can include any network capable of carrying data, including the Internet, Ethernet, local area network, wide area network, and others, including any combination of these, capable of interfacing with, and enabling communication.

Figure 11C:
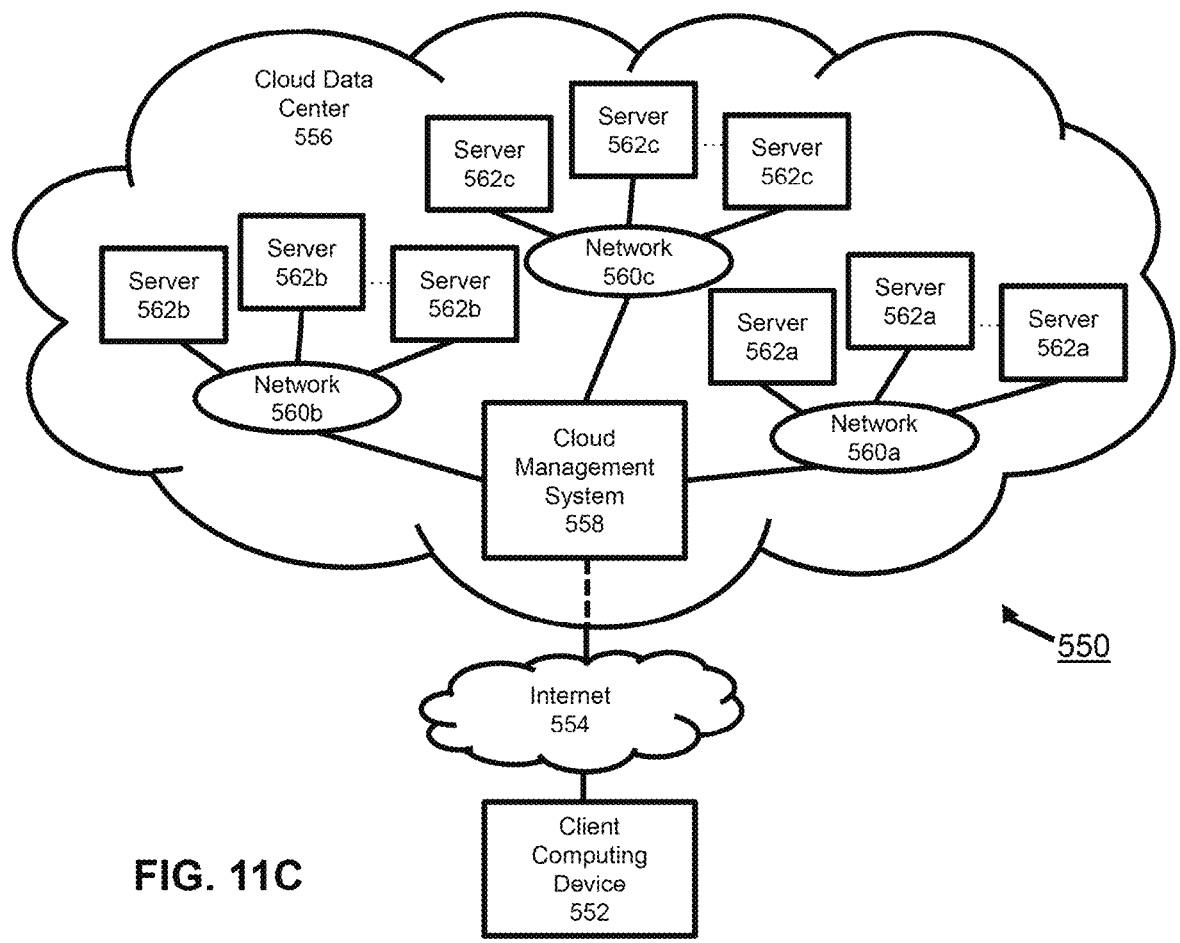
FIG. 11C is an exemplary cloud computing system that may be used for implementation of all or a portion of the invention.

Separate and apart from, or in addition to, computer system 500 and computing system 580, the methods according to the invention may be implemented using a cloud computing system. FIG. 11C illustrates an exemplary cloud computing system 550 that may be used to implement the methods according to the invention. The cloud computing system 550 includes a plurality of interconnected computing environments. The cloud computing system 550 utilizes the resources from various networks as a collective virtual computer, where the services and applications can run independently from a particular computer or server configuration making hardware less important.

Specifically, the cloud computing system 550 includes at least one client computer 552. The client computer 552 may be any device through the use of which a distributed computing environment may be accessed to perform the methods disclosed herein, for example, the computer described above in FIG. 11A, a portable computer, mobile phone, personal digital assistant, tablet to name a few. Signals are transferred between the client computer 552 and external devices including networks such as the Internet 554 and cloud data center 556. Communication may be implemented using wireless or wired capability such as cable, fiber optics, a phone line, a cellular phone link, radio waves or other communication channels.

The client computer 552 establishes communication with the Internet 554—specifically to one or more servers—to, in turn, establish communication with one or more cloud data centers 556. A cloud data center 556 includes one or more networks 560a, 560b, 560c managed through a cloud management system 558. Each network 560a, 560b, 560c includes resource servers 562a, 562b, 562c, respectively. Servers 562a, 362b, 362c permit access to a collection of computing resources and components that can be invoked to instantiate a virtual computer, process, or other resource for a limited or defined duration. For example, one group of resource servers can host and serve an operating system or components thereof to deliver and instantiate a virtual computer. Another group of resource servers can accept requests to host computing cycles or processor time, to supply a defined level of processing power for a virtual computer. A further group of resource servers can host and serve applications to load on an instantiation of a virtual computer, such as an email client, a browser application, a messaging application, or other applications or software.

The cloud management system 558 may be configured to query and identify the computing resources and components managed by the set of resource servers 562a, 562b, 562c needed and available for use in the cloud data center 556. Specifically, the cloud management system 558 may be configured to identify the hardware resources and components such as type and amount of processing power, type and amount of memory, type and amount of storage, type and amount of network bandwidth and the like, of the set of resource servers 562a, 562b, 562c needed and available for use in the cloud data center 556. Likewise, the cloud management system 558 can be configured to identify the software resources and components, such as type of Operating System ("OS"), application programs, and the like, of the set of resource servers 562a, 562b, 362c needed and available for use in the cloud data center 556.

The cloud computing system 550 of FIG. 10 is provided only for purposes of illustration and does not limit the invention to this specific embodiment. It is appreciated that a person skilled in the relevant art knows how to program and implement the invention using any computer system or network architecture.

While the invention is susceptible to various modifications and alternative forms, specific exemplary embodiments of the invention have been shown by way of example in the drawings and have been described in detail. It should be understood, however, that there is no intent to limit the invention to the particular embodiments disclosed, but on the contrary, the intention is to cover all modifications, equivalents, and alternatives falling within the scope of the invention as defined by the appended claims.

The invention claimed is:

1. A computer program stored in one or more non-transitory computer-readable mediums for generating a profile identifying a state of a subject gut microbiome and gut maturity, the computer program comprising instructions for performing the steps of:

accessing by a processor microbiome and gut microbiome maturity measure ("GM3") information of a subject, the GM3 information consisting of categories: (a) non-modifiable risk factors, (b) modifiable risk factors, (c) perinatal and maternal risk factors, and (d) microbiome-based measures of gut status;

transforming the GM3 information into a gut maturity/readiness profile of the state of the subject gut microbiome and gut maturity, wherein the transforming step further comprises the steps of, providing by the processor an equation: GM3 value=$f_1 w_1 + f_2 w_2 + f_3 w_3 + f_x w_x$, wherein "f" is a factor within the categories of the GM3 information and "w" is a weight value, wherein each weight value corresponds to an impact of the factor on a GM3 score, and calculating by the processor a subject GM3 value using the GM3 information of the subject; and displaying by the processor on a display a graphical user interface summarizing a state of the subject's gut maturity/readiness profile, wherein the graphical user interface comprises a plurality of charts and a plurality of concentric circles, wherein with each chart of the plurality has the same x-axis representing a number of days of life for the subject, and the plurality incudes a bar chart and a bar graph, the bar chart including a y-axis representing a feed rate value of the subject, the bar chart including a plurality of first rectangles, wherein each first rectangle comprises one or more segments, each segment comprising a height and a color, wherein the color is representative of a type of feed comprising breast milk ("MBM"), donor's breast milk ("DBM"), or formula ("FORM"), and the height is representative of the feed rate value of the subject;

the bar graph including a y-axis representing a proportion value of a microbiota of the subject, the bar graph including a plurality of second rectangles, wherein each second rectangle comprises one or more portions, each portion comprising a height and a color, wherein the color identifies a type of microbiota and the height is representative of a value for a proportion of the type of microbiota with respect to other microbiota, wherein the gut maturity/readiness profile is configured to assist with decision making relating to nutrition or care for the subject; and, wherein the plurality of concentric circles form a center circle that includes a calculated subject GM3 value, a first annulus that includes a plurality of pie chart elements, and a second annulus that identifies the factors, a size of each pie chart elements representative of the weight value of the corresponding factor on the GM3 value, each pie chart element including a bar chart element representative of an impact of the factor on the calculated subject GM3 value.

2. The computer program according to claim 1, further comprising a line chart directed to "Microbiota for Age Z-Score", the line chart with a y-axis representing a "Z-score" of the subject, the line chart including a plurality of points, wherein each point comprises a value for microbiota for an age of the subject with respect to a mean for a group of 'healthy' subjects at the same age and at the same day of life.

3. The computer program according to claim 1, further comprising a line chart with a second y-axis representing a gut community type, wherein the line chart indicates a stage of a gut community type ("GCT").

4. The computer program according to claim 1, further comprising a line chart with a second y-axis representing a "weighted Z-score", wherein the line chart indicates a weighted z-score describing a feed rate value compared to a mean for a group of feed rate values.

5. The computer program according to claim 1, wherein the factors identified in the second annulus for the non-modifiable risk factors category includes the factors: mode of birth, chronological or, in the case of a preterm infant gestational, age at birth, and gastrointestinal disease.

6. The computer program according to claim 1, wherein the factors identified in the second annulus for the perinatal and material risk factors category includes the factors: maternal diet, mother body mass index (BMI), perinatal steroid and antibiotic exposure, and maternal age.

7. The computer program according to claim 1, wherein the factors identified in the second annulus for the modifiable risk factors category includes the factors: nutrition, diet, antibiotic administration, and pre-/probiotics administration.

8. The computer program according to claim 1, wherein the factors identified in the second annulus for the microbiome-based measures of gut status category includes the factors: classification, stability, maturity.

9. The computer program according to claim 1, further comprising the steps of:
   selecting by the processor a protocol from a plurality of protocols, wherein the selected protocol corresponds to the gut maturity/readiness profile; and
   displaying by the processor on the display or aurally communicating the selected protocol.

10. The computer program according to claim 1, wherein the display includes a section providing "Birth and Growth Measures" comprising information for the subject including delivery mode, sex, weight, and a section providing "Predictive Measures" comprising one or more risk predictions of growth failure and non-typical development based on applying artificial intelligence/machine learning algorithms on clinical and/or microbiome data, at different time periods as well as actual growth and development.

11. The computer program according to claim 1, wherein a graph "Events, Fortification, Antibiotics" comprises icons such as circles, diamonds, squares, triangles representing one or more nutritional milestones, diagnoses, treatments, or occurrences comprising: return to birthweight ("RTBW"), Retinopathy of prematurity ("ROP"), Bronchopulmonary dysplasia ("BPD").

* * * * *